US010183912B2

(12) United States Patent
Wald et al.

(10) Patent No.: US 10,183,912 B2
(45) Date of Patent: Jan. 22, 2019

(54) HDMX INHIBITORS AND THEIR USE FOR CANCER TREATMENT

(71) Applicant: MIRX PHARMACEUTICALS, LLC, Lexington, KY (US)

(72) Inventors: David Wald, Shaker Heights, OH (US); Mukesh Agarwal, Solon, OH (US); Zhiqing Xia, Lexington, KY (US); Goutam Karan, Lexington, KY (US); Mahesh Gundluru, Louisville, KY (US)

(73) Assignee: MIRX PHARMACEUTICALS, LLC, Lexington, KY (US)

(*) Notice: Subject to any disclaimer, the term of this patent is extended or adjusted under 35 U.S.C. 154(b) by 0 days.

(21) Appl. No.: 15/300,871

(22) PCT Filed: Mar. 31, 2015

(86) PCT No.: PCT/US2015/023462
§ 371 (c)(1),
(2) Date: Sep. 30, 2016

(87) PCT Pub. No.: WO2015/153535
PCT Pub. Date: Oct. 8, 2015

(65) Prior Publication Data
US 2017/0022166 A1  Jan. 26, 2017

Related U.S. Application Data

(60) Provisional application No. 61/972,514, filed on Mar. 31, 2014.

(51) Int. Cl.
| *C07D 219/02* | (2006.01) |
| *A61K 31/473* | (2006.01) |
| *A61K 31/496* | (2006.01) |
| *A61K 45/06*  | (2006.01) |
| *C07D 219/08* | (2006.01) |
| *C07D 219/10* | (2006.01) |
| *C07D 219/12* | (2006.01) |
| *C07D 401/12* | (2006.01) |
| *C07D 401/14* | (2006.01) |
| *C07D 417/12* | (2006.01) |
| *C07D 495/04* | (2006.01) |

(52) U.S. Cl.
CPC .......... *C07D 219/02* (2013.01); *A61K 31/473* (2013.01); *A61K 31/496* (2013.01); *A61K 45/06* (2013.01); *C07D 219/08* (2013.01); *C07D 219/10* (2013.01); *C07D 219/12* (2013.01); *C07D 401/12* (2013.01); *C07D 401/14* (2013.01); *C07D 417/12* (2013.01); *C07D 495/04* (2013.01)

(58) Field of Classification Search
CPC .. C07D 219/02; C07D 219/08; C07D 219/10; C07D 219/12; C07D 401/12; C07D 401/14; C07D 417/12; C07D 495/04; A61K 31/473; A61K 31/496; A61K 45/06
USPC .................................................... 514/253.03
See application file for complete search history.

(56) References Cited

U.S. PATENT DOCUMENTS

| 2007/0015235 A1 | 1/2007 | Mayer et al. |
| 2008/0161324 A1 | 7/2008 | Johansen et al. |
| 2012/0220537 A1 | 8/2012 | Gellerman |

FOREIGN PATENT DOCUMENTS

| WO | 2001/64645 A2 | 9/2001 |
| WO | 2008010984 A2 | 1/2008 |

OTHER PUBLICATIONS

STN Registry of 3,6-diamino-9-acridinecarbonitrile RN: 501935-96-2 date entered: Jan. 7, 2003.*
Denny, W. A., et al: "Potential antitumor agents. 26. Quantitative relationships between experimental antitumor activity, toxicity, and structure for the general class of 9-anilinoacridine antitumor agents", Journal of Medicinal Chemistry, American Chemical Society, vol. 25, No. 3, Mar. 1, 1982 (Mar. 1, 1982), pp. 276-315.
Klopman, G., et al: "Computer-Automated Structure Evaluation of Antileukemic 9-Anilinoacridines", Molecular Pharmacology, American Society for Pharmacology and Experimental Therapeutics, US, vol. 31, No. 4, Jan. 1, 1987 (Jan. 1, 1987), pp. 457-476.
Loza-Mejia, M. A., et al: "Molecular modeling of tricyclic compounds with anilino substituents and their intercalation complexes with DNA sequences", Journal of Molecular Graphics and Modelling, Elsevier Science, New York, NY, vol. 27, No. 8, Jun. 1, 2009 (Jun. 1, 2009), pp. 900-907.
Mauel, J., et al: "9-Anilinoacridines as Potential Antileishmanial Agents", Antimicrobial Agents and Chemotherapy, American Society for Microbiology, vol. 37, No. 5, May 1, 1993 (May 1, 1993-05-01), pp. 991-996.
Werbovetz, K. A., et al: "Cleavable complex formation in Leishmania chagasi treated Iwith anilinoacridines", Molecular and Biochemical Parasitology, Elsevier Science Publishers, Amsterdam, NL, vol. 65, No. 1, May 1, 1994 (May 1, 1994), pp. 1-10.
Gao, Hua, et al: "Quantitative structure-activity relationships (QSAR) for 9-anilinoacridines: a comparative analysis", Chemico-Biological Interactions, vol. 116, No. 3, Nov. 1, 1998 (Nov. 1, 1998), pp. 157-180.
Wroblewska, Agnieszka, et al: "Tautomerism of 9-acridinamines substituted at the exocyclic nitrogen atom in view of computational predictions and experimental findings". Chemical Physics, vol. 303, No. 3, Aug. 1, 2004 (Aug. 1, 2004). pp. 301-308.

(Continued)

*Primary Examiner* — Yevgeny Valenrod
(74) *Attorney, Agent, or Firm* — King & Schickli, PLLC

(57) ABSTRACT

The present invention provides for novel acridine-like class of compounds that have demonstrated efficiency in treating cancer. The compounds of the present invention have demonstrated efficacy in binding to and antagonizing the activity of the p53 repressor, HDMX. Once administered to a cell, the compounds of the present invention bind HDMX, thereby allowing p53 to induce apoptosis of the cancerous cell. A combination of this class of compounds along with Nutlin3 provides a novel approach to treat cancers.

14 Claims, 8 Drawing Sheets

(56) References Cited

OTHER PUBLICATIONS

Figure 1:
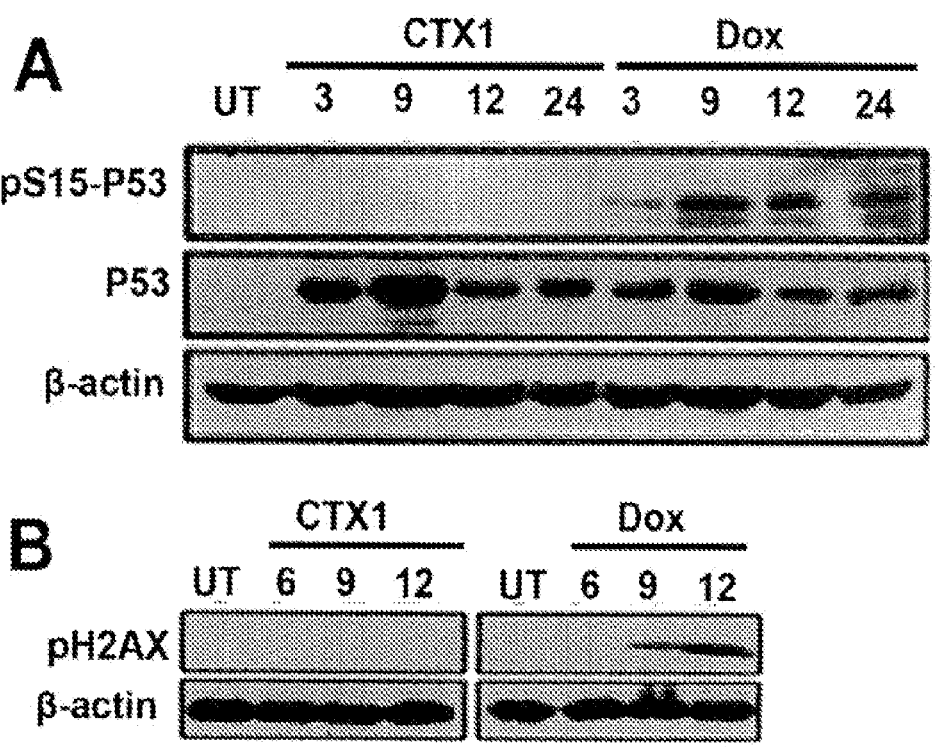

Martin, Roger F., et al.: "Synthesis and N.M.R. Spectra of Substituted Aminoiodoacridines", Australian Journal of Chemistry: An International Journal for Chemical Science, vol. 32, No. 12, Jan. 1, 1979 (Jan. 1, 1979), p. 2637-46.

Kawamura, Kazunori, et al: "In Vivo Evaluation of Limiting Brain Penetration of Probes for [alpha] 2C-Adrenoceptor Using Small-Animal Positron Emission Tomography", ACS Chemical Neuroscience, vol. I, No. 7, Jul. 21, 2010 (Jul. 21, 2010), pp. 520-528.

Chavalitshewinkoon-Petmitr, P., et al: "Inhibitory effects of 9-anilinoacridines on Plasmodium falciparum gametocytes", Tropical Medicine and International Health, vol. 6, No. I, Jan. 1, 2001 (Jan. 1, 2001) pp. 42-45.

* cited by examiner

FIGURE 2
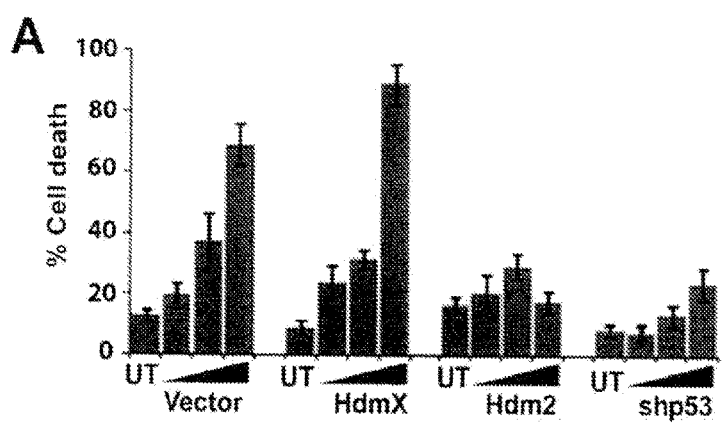
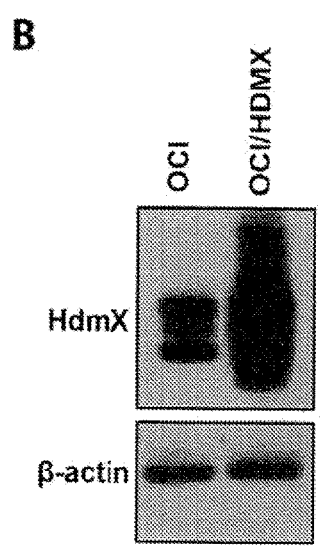
| LD$_{50}$ (µM) | OCI-AML | OCI/HdmX |
|---|---|---|
| CTX1 | 0.97 | 0.78 |
| Nutlin3 | 8.9 | 12.7 |

HDMX INHIBITORS AND THEIR USE FOR CANCER TREATMENT

RELATED APPLICATIONS

This application claims priority to U.S. Provisional Application 61/972,514, filed Mar. 31, 2014, which is hereby incorporated in its entirety.

FIELD OF INVENTION

The present application relates to the synthesis of small molecule compounds derived from INVA3Z-2-1 (CTX1) that exhibit strong antagonistic activity with low toxicity to cancers involving aberrant p53, HDMX, and HDM2 activity.

BACKGROUND OF THE INVENTION:

The majority of the cancer therapeutics act in a relatively nonspecific fashion to kill rapidly dividing cancer cells, often through DNA damage that can lead to significant toxicities or other complications. Recently, drugs that target specific protein-protein or protein-RNA interactions became more attractive as they offer several advantages with regard to efficacy and toxicity. In normal cellular physiology, p53 functions as a tumor suppressor protein that plays a central role in controlling cell cycle progression and apoptosis. Due to this critical role, p53 is considered as an attractive cancer therapeutic target because stimulating its tumor suppressor activity can potentially eradicate tumor cell growth. The present invention presents a novel class of chemicals that targets the protein called HDMX. HDMX physiologically plays major role in survival of cancer cells. In normal cellular conditions, p53 is negatively regulated by both HDMX and HDM2 proteins. It has been demonstrated that Nutlin-3 induced inhibition of HDM2 causes cell death by inducing p53, independent of DNA damage. A variant of Nutlin-3 is currently undergoing clinical trials; however, use of these analogs is limited as they do not affect HDMX which suppresses p53 in a much large subset of cancer cells than HDM2. HDMX, a structural homolog of HDM2, can be successfully targeted by the compounds of the present invention and induce cell cycle arrest and subsequently cause apoptotic cell death. In the present invention, the structures and synthesis of these compounds are presented as well as analysis of activity in disrupting p53-HDMX interactions that are based on the acridine scaffold.

SUMMARY OF THE INVENTION

The present invention provides for composition of matter of compounds depicted in formula I and II that demonstrate strong anticancer property towards various cancer cell lines in a non DNA damaging pathway. Data compiled from administering the compounds to cells demonstrate that the compounds in formula I and II act as HDMX inhibitors and can be beneficial to treat any type of cancer associated with HDMX, HDM2 and p53. In particular, compounds INVA3Z-2-1 (CTX1) and INVA3Z-50-2 (CTX50) showed strong binding affinity towards HDMX protein therefore leading cancer cell towards terminal differentiation. The compounds of the present invention comprise the structure:

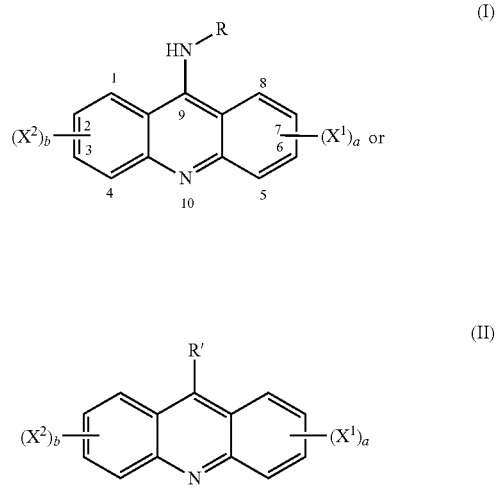

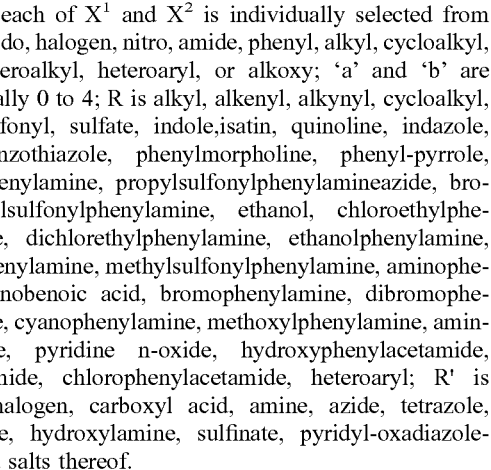

wherein each of $X^1$ and $X^2$ is individually selected from cyano, iodo, halogen, nitro, amide, phenyl, alkyl, cycloalkyl, aryl, heteroalkyl, heteroaryl, or alkoxy; 'a' and 'b' are individually 0 to 4; R is alkyl, alkenyl, alkynyl, cycloalkyl, aryl, sulfonyl, sulfate, indole,isatin, quinoline, indazole, aminobenzothiazole, phenylmorpholine, phenyl-pyrrole, aminophenylamine, propylsulfonylphenylamineazide, bromopropylsulfonylphenylamine, ethanol, chloroethylphenylamine, dichlorethylphenylamine, ethanolphenylamine, biotinphenylamine, methylsulfonylphenylamine, aminophenol, aminobenoic acid, bromophenylamine, dibromophenylamine, cyanophenylamine, methoxylphenylamine, aminopyridine, pyridine n-oxide, hydroxyphenylacetamide, phenylamide, chlorophenylacetamide, heteroaryl; R' is cyano, halogen, carboxyl acid, amine, azide, tetrazole, hydrazine, hydroxylamine, sulfinate, pyridyl-oxadiazole-thiol and salts thereof.

In particular, the compounds of the present invention comprise a structure selected from the group consisting of:

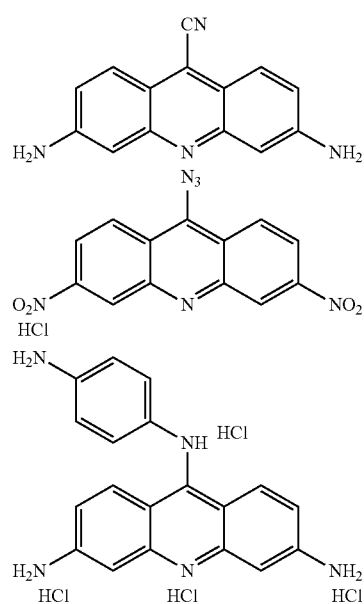

-continued
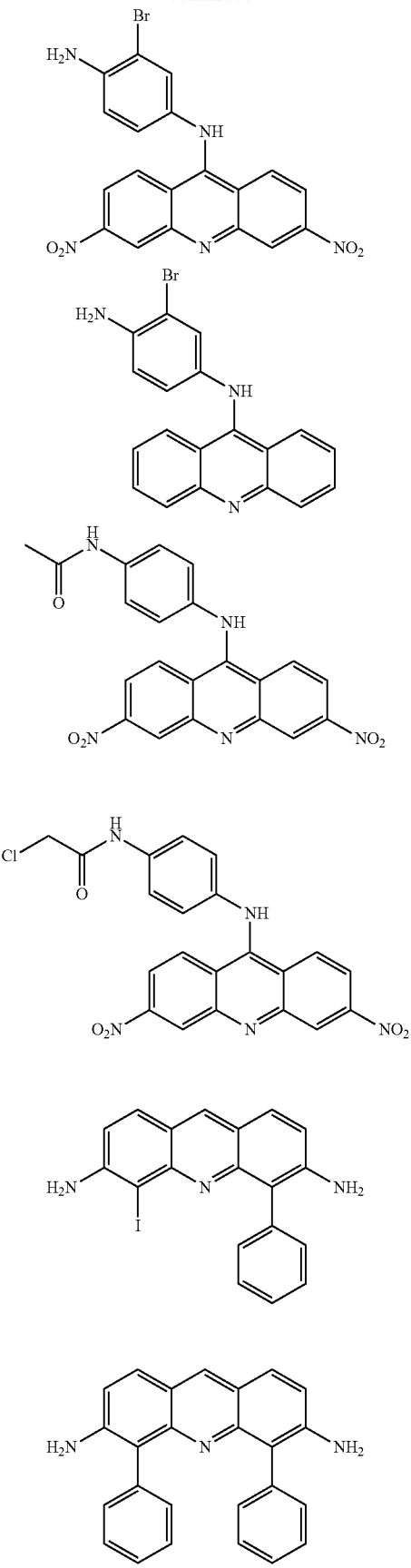
-continued
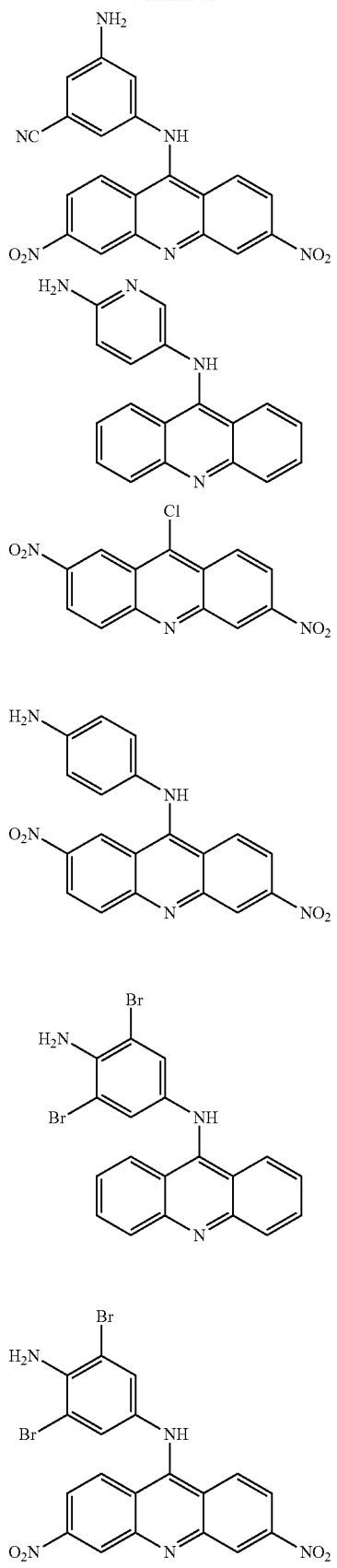

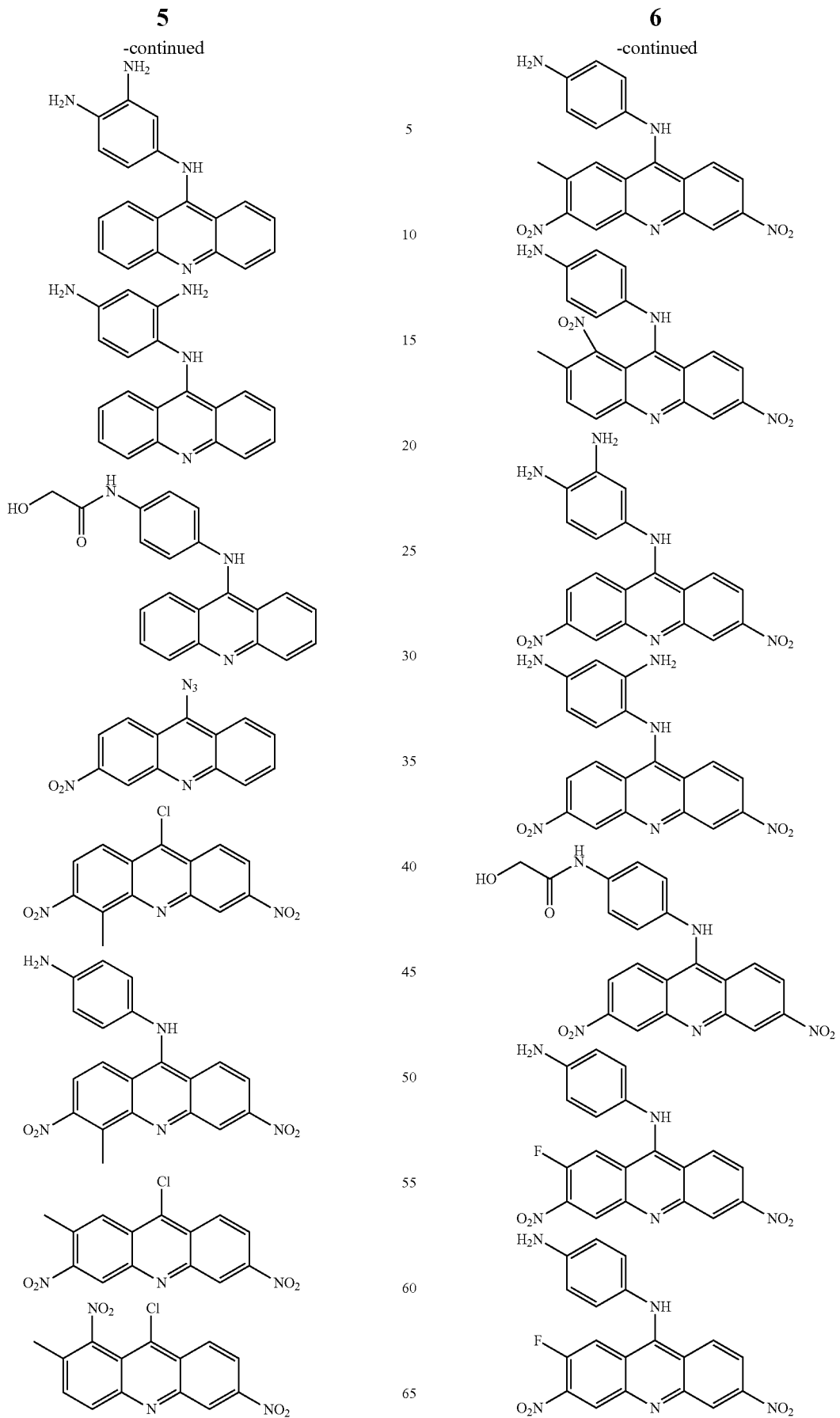

-continued
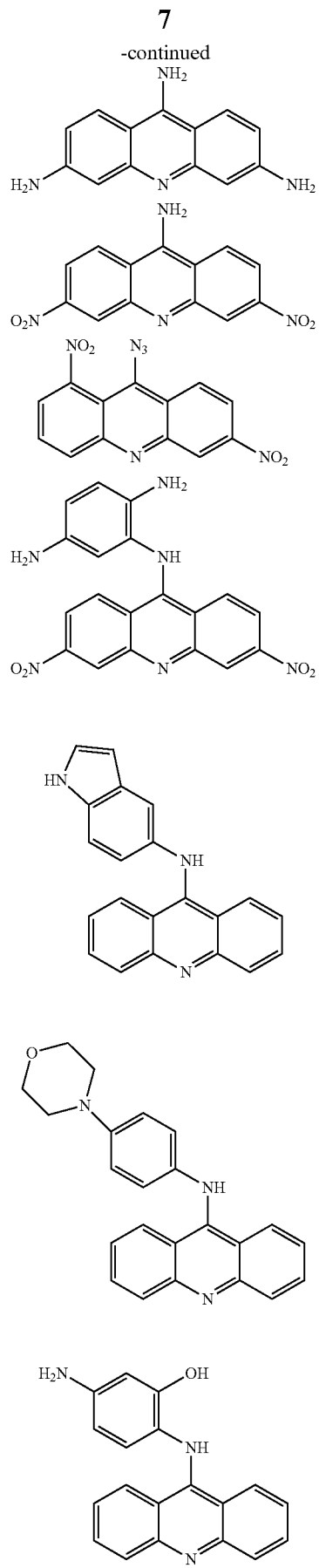
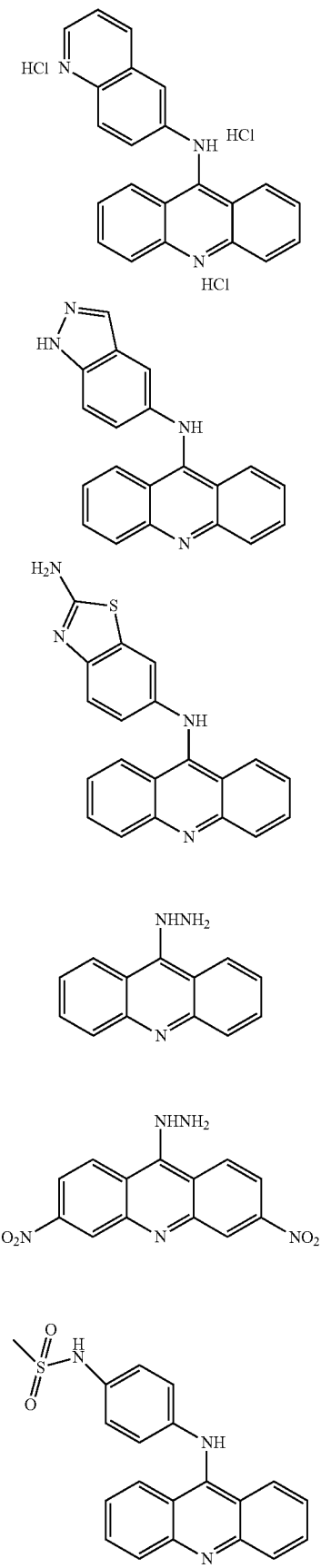

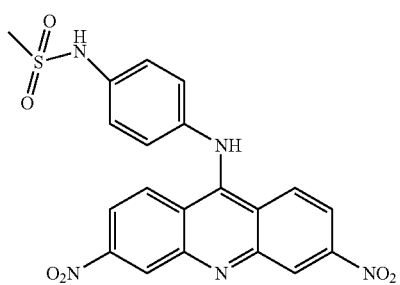
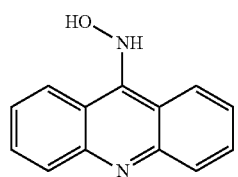
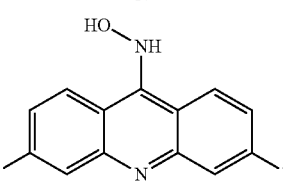
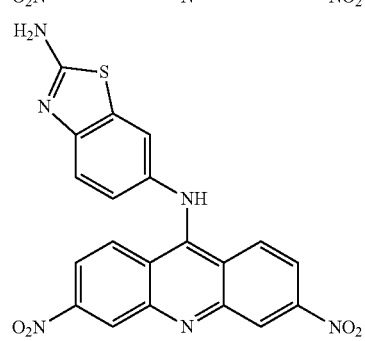
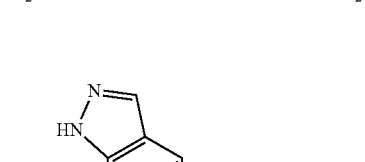
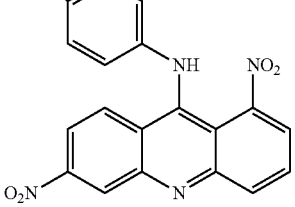
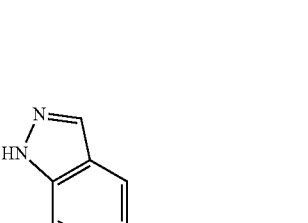
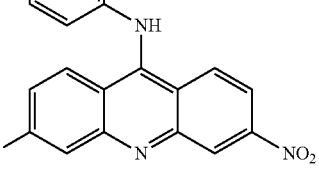
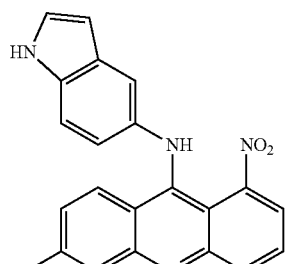
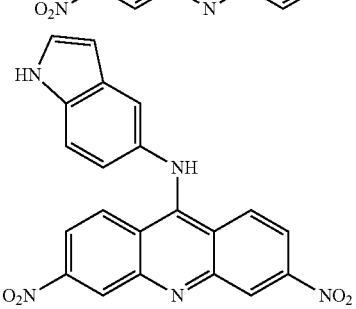
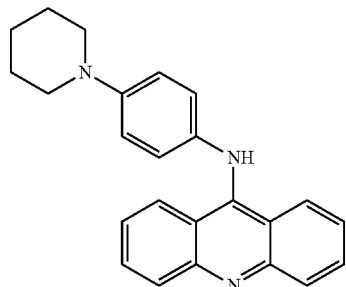
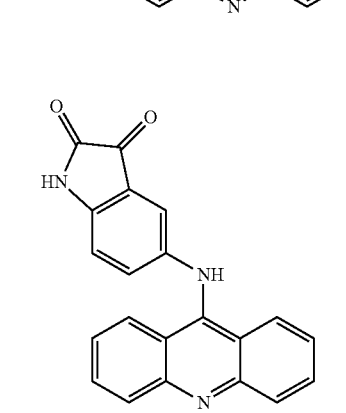
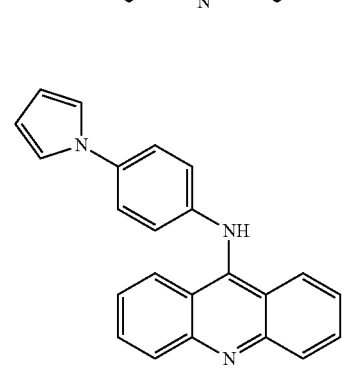

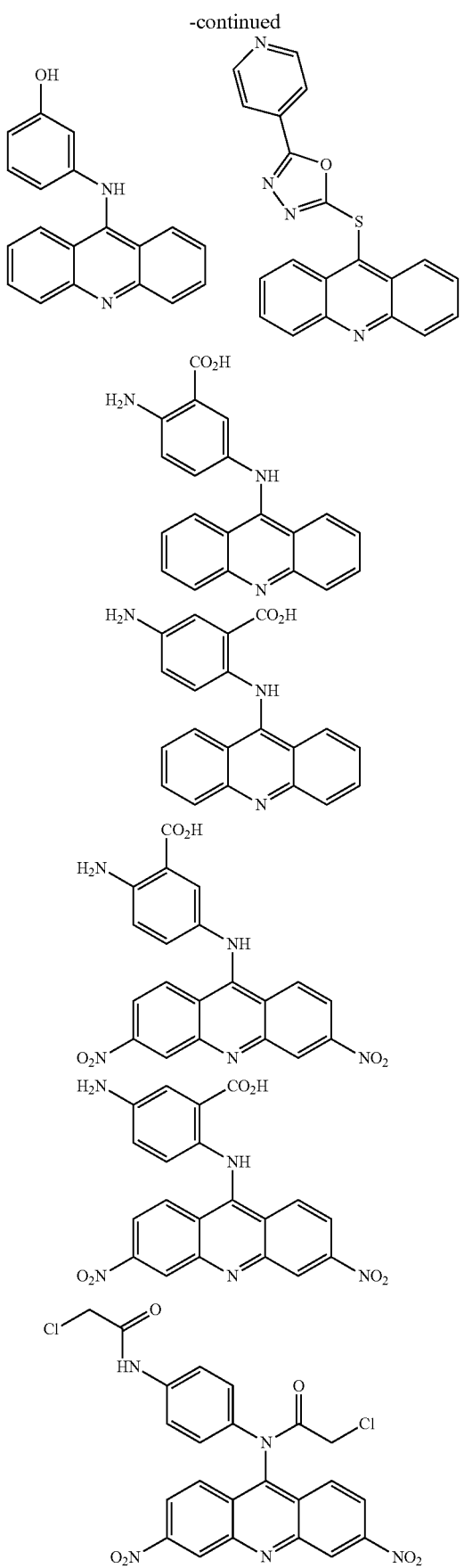
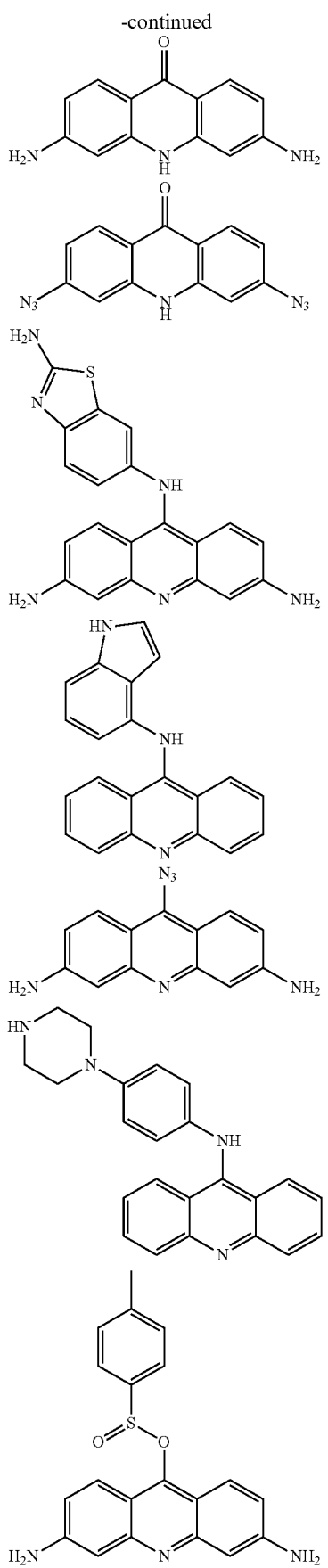

-continued
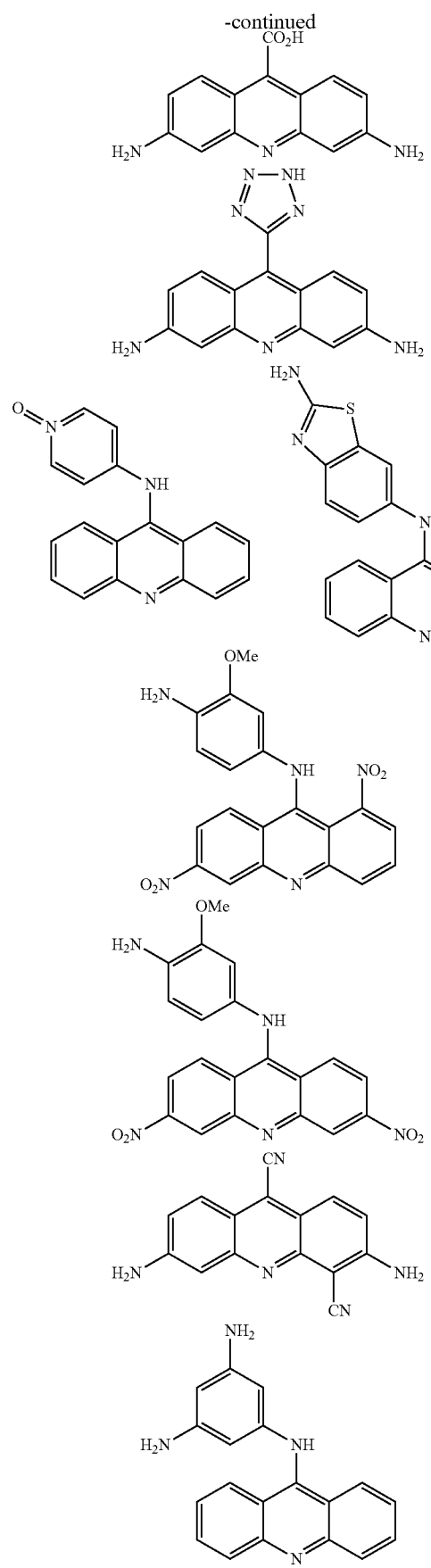
-continued
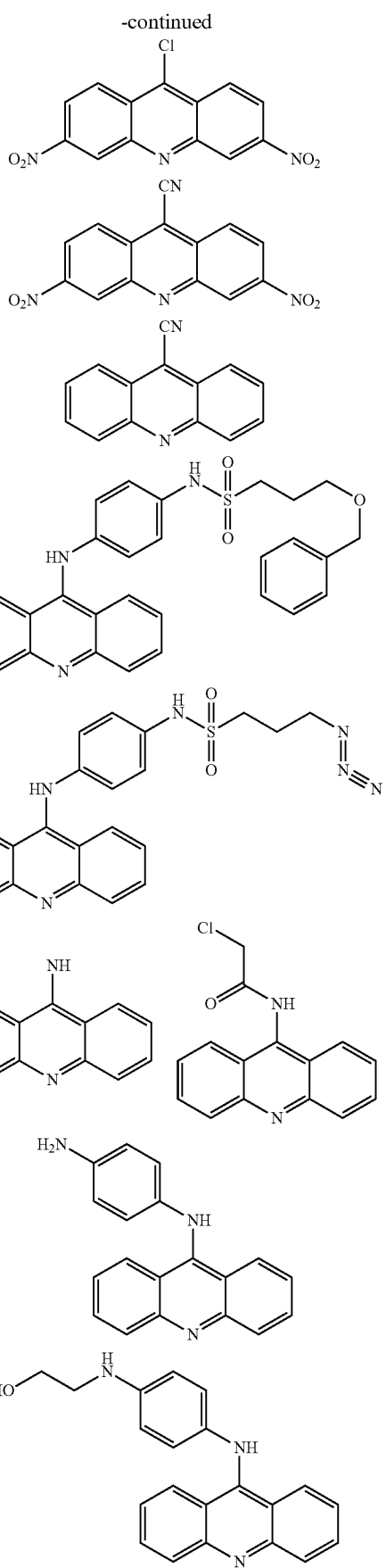

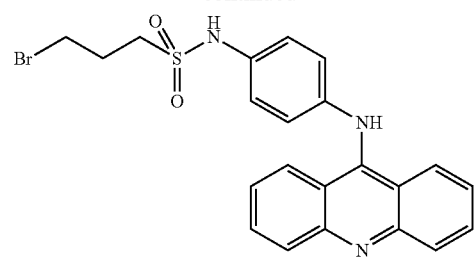
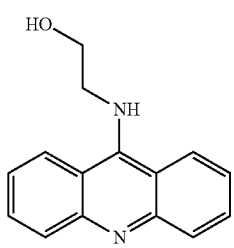
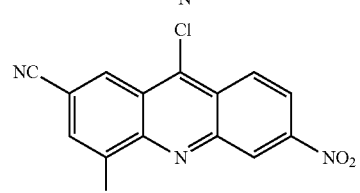
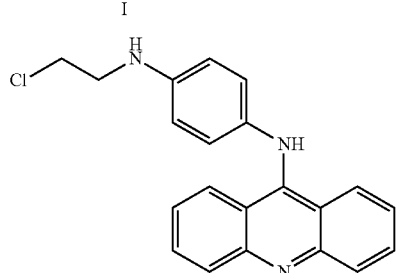
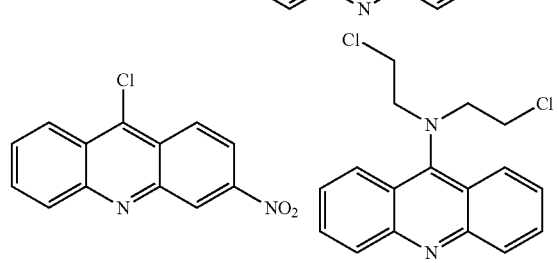
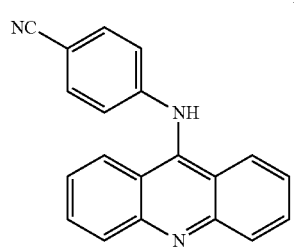
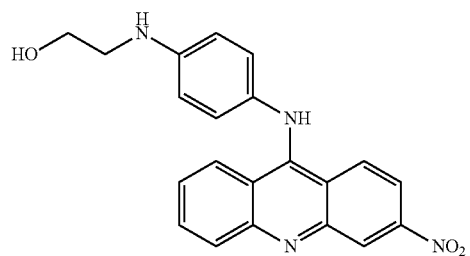
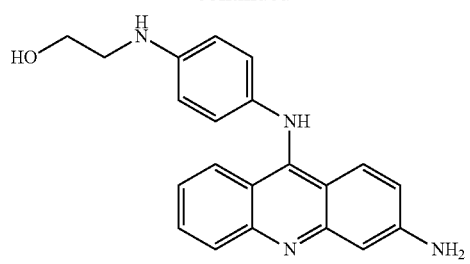
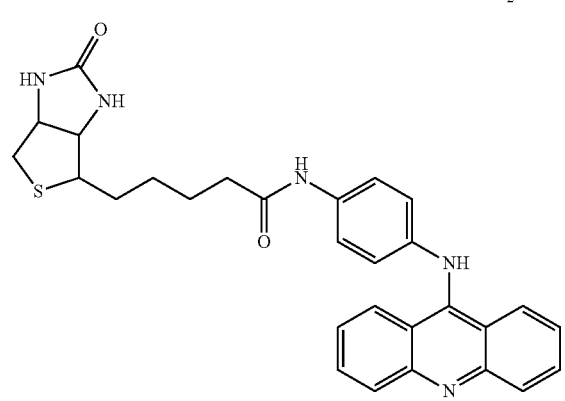
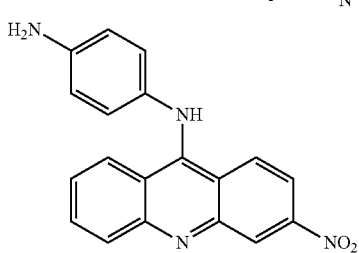
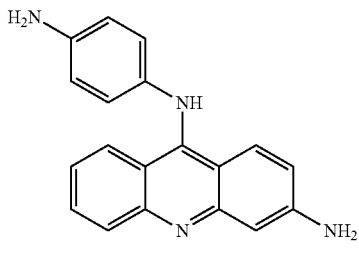
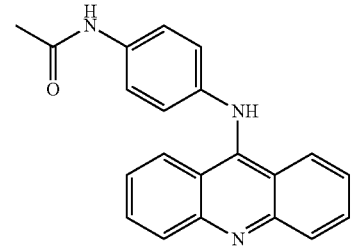
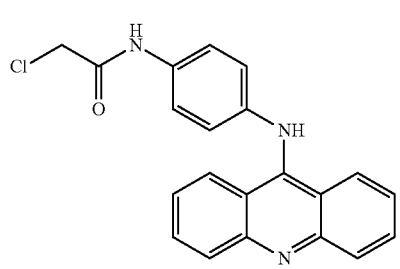

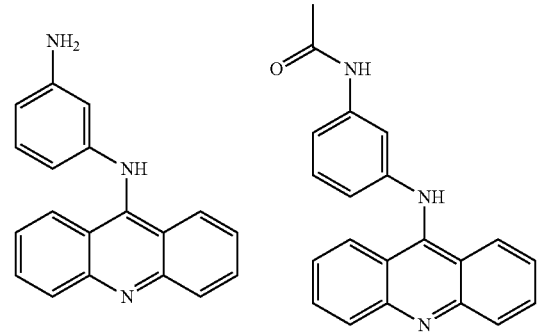
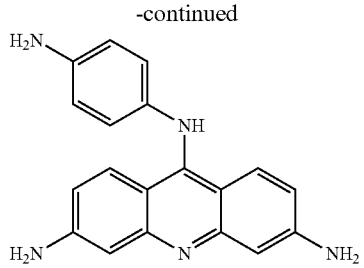
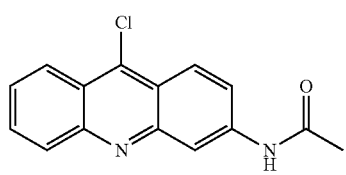
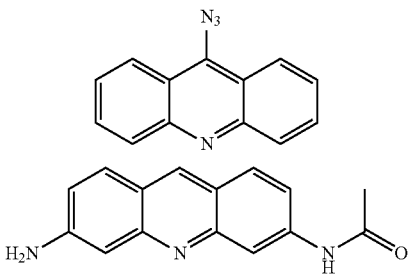
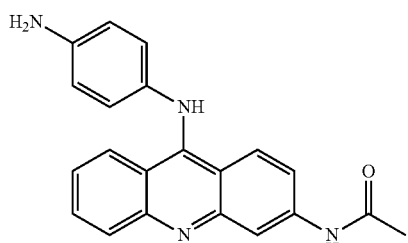
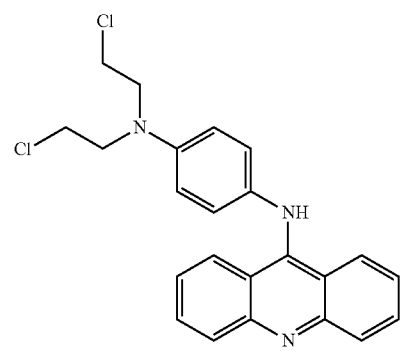
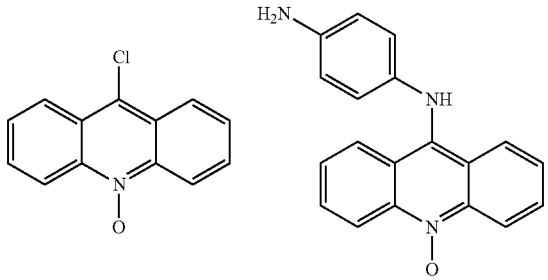
5 HCl
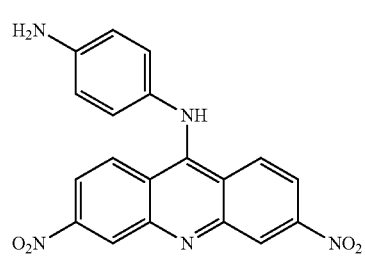
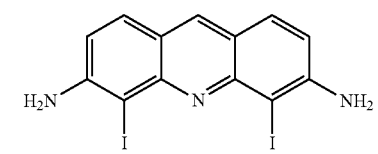
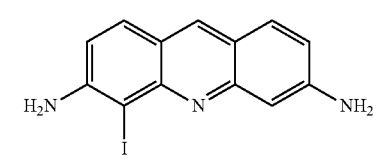
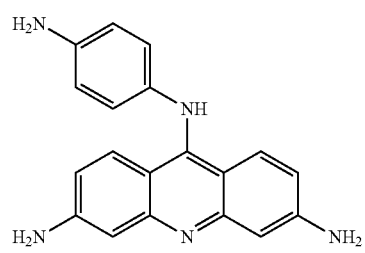
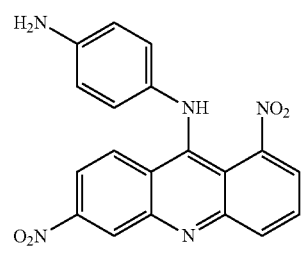

-continued

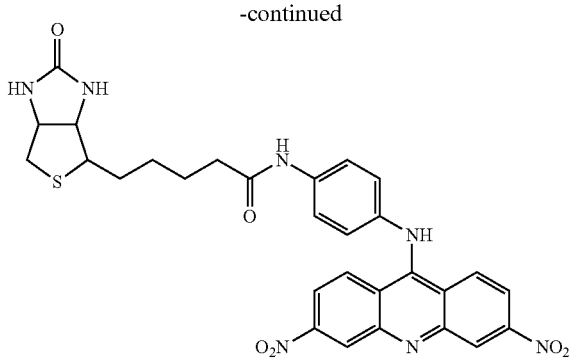

and salts thereof.

In certain embodiments, the structure is

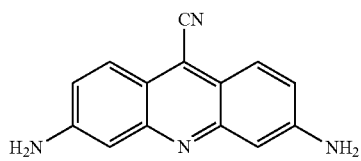 [SMILES: N#Cc1c2ccc(N)cc2nc2cc(N)ccc12]

or a salt thereof.

In other embodiments, the structure is

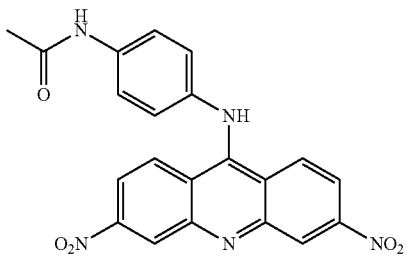

or a salt thereof.

The present invention also provides for pharmaceutical compounds comprising the compounds and a pharmaceutically acceptable carrier.

The present invention also provides methods of inducing apoptosis in a cell, comprising administering the compounds of to a cell, wherein the compound antagonizes HDMX activity toward p53. The cell may be within a subject. The methods may comprise selecting for increased HDMX and/or HDM2 activity within the cell, as well as for decreased p53 activity. In some instances, the compounds may be administered with nutlin-3, such as where HDM2 activity is also elevated.

The present invention further provides methods of treating a cancerous cell comprising administering the compounds of to a cancerous cell. The cancerous cell may be within a subject, such as a human. The compound may be administered by inhalation, injection or oral administration. The cancerous cell may be selected for reduced p53 activity and/or increased HDMX activity. The compound may be administered in combination with nutlin-3 or another chemotherapeutic agent.

BRIEF DESCRIPTION OF FIGURES AND DRAWINGS

FIG. 1 shows that CTX1 rapidly induces p53 independent of DNA damage. MCF7 cells were treated with CTX1 (3 µM) or Doxorubicin (1 µM) for the indicated times (hours) and western analysis was performed for markers of DNA damage (p-p53 (Ser15) and p-H2AX).

FIG. 2 shows that CTX1 specifically targets and directly binds to HDMX. A) CTX1 preferentially kills cells transformed by HDMX and not HDM2 or shp53. IMR90 cells overexpressing the indicated constructs were treated with increasing doses of CTX1 (1, 2.5 and 5 µM) and assessed for cell death at 72 hr by trypan blue staining. B-C) HDMX overexpression does not impair CTX1-mediated killing in leukemia cells. B) HDMX overexpression in OCI cells. Western analysis demonstrating HDMX overexpression in OCI/HDMX cells. C). HDMX overexpression does not impair CTX1 killing of OCI cells. The indicated cells were treated with increasing doses of CTX1 or nutlin-3 and the $LD_{50}$ was calculated by measuring cell death at 72 hr using trypan blue.

Figure 3:
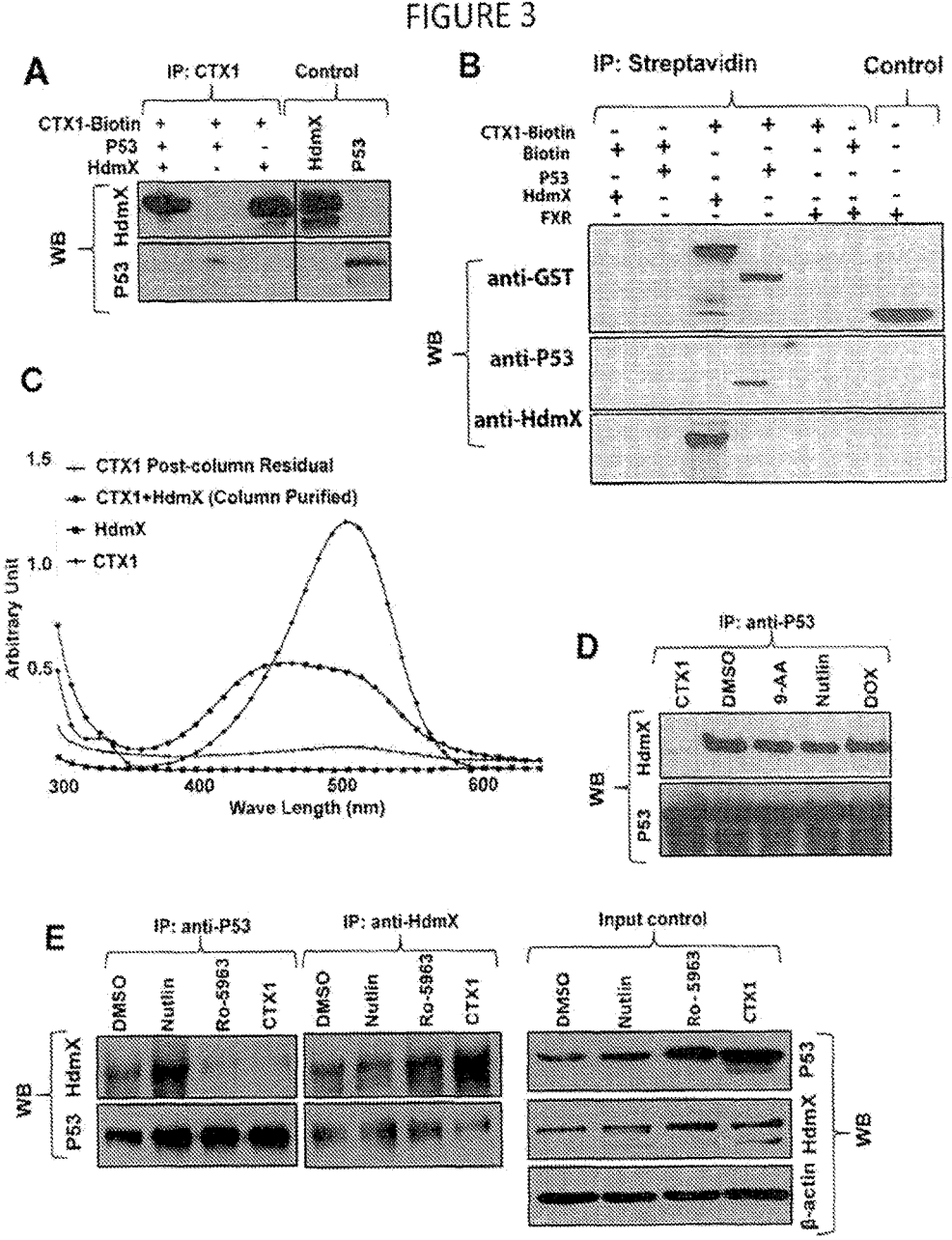

FIG. 3 shows that CTX1 specifically targets and directly binds to HDMX. A) CTX1 binds HDMX and to a lesser extent p53. Recombinant p53, HDMX, and/or biotin-CTX1 were incubated in vitro and streptavidin beads were used to pull down the protein complex. The bound protein was eluted and analyzed by western blot with the indicated antibodies. B) Biotin and unrelated GST tagged proteins such as FXR do not bind HDMX. C) Spectral studies suggest CTX1 and HDMX directly interact. CTX1 and HDMX alone represent the spectral pattern of both agents without purification. The CTX1+HDMX sample and CTX1 Postcolumn Residual samples underwent size exclusion chromatography to remove unbound CTX1. D-E) CTX1 disrupts the interaction of recombinant HDMX/p53 but not HDM2/p53 by co-immunoprecipitation. The indicated drugs were used as controls. CTX1 disrupts the interaction of HDMX/p53 in cells. Immunoprecipitations were performed as indicated using lysate from OCI cells treated with the indicated drugs or a DMSO control.

Figure 4:
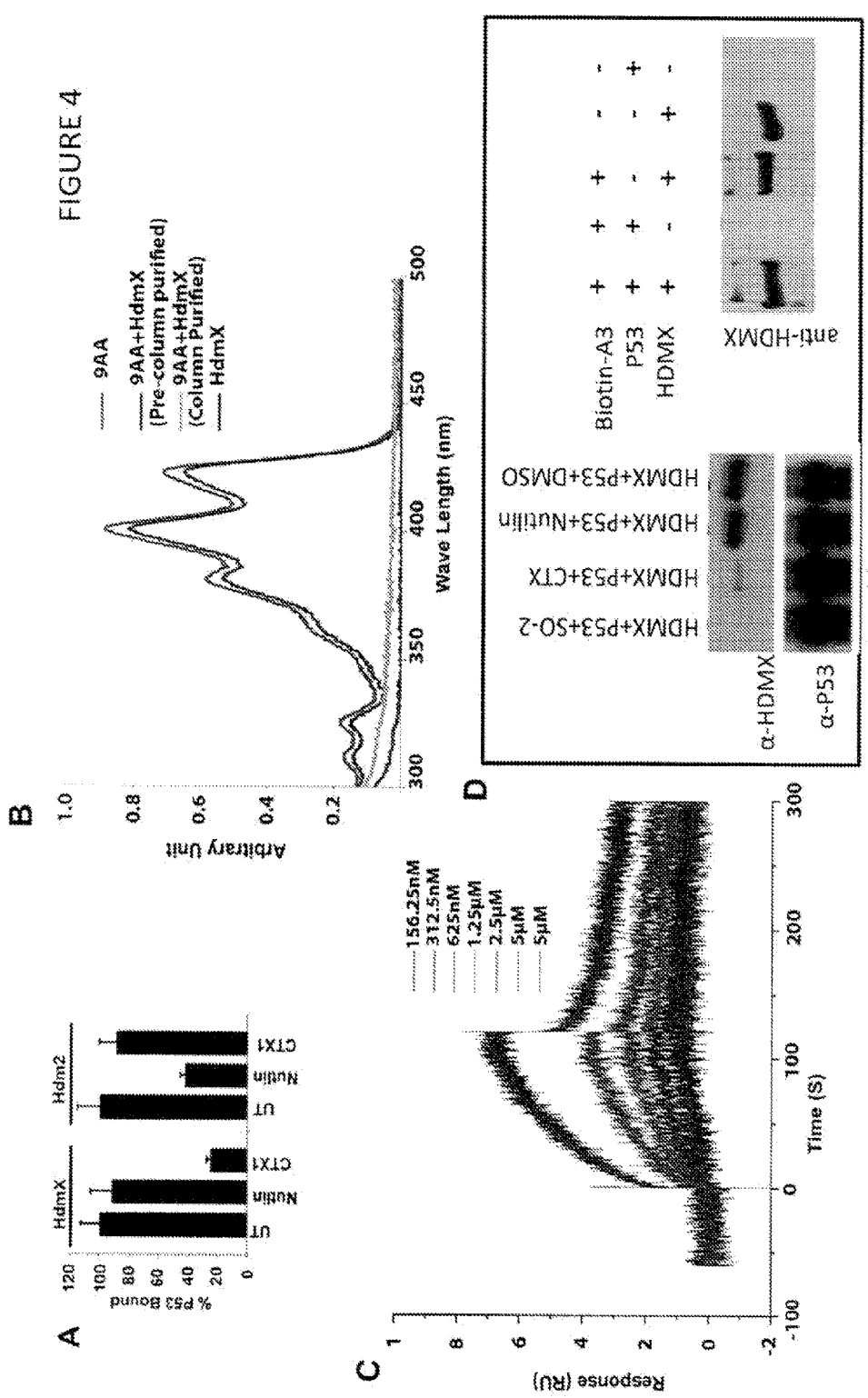

FIG. 4 shows that CTX1 specifically interacts with HDMX. A) CTX1 disrupts the interaction of recombinant HDMX/p53 but not HDM2/p53 by ELISA. B) Spectral studies do not support an interaction of 9-AA and HDMX. Spectral studies were performed using 9-AA. C) Surface Plasmon Resonance studies suggest HDMX interacts directly with CTX1. A dose curve of CTX1 was tested for binding by SPR against immobilized recombinant HDMX. D) Co-immunoprecipitation of P53 and HDMX in presence or absence of CTX1 or CTX50 or Nutlin3 followed by WB\blot analysis of respective antibody to find the presence of protein in each reaction mixture. Only CTX1 and CTX50 disrupts P53-HDMX protein interaction compare to control DMSO and know MDM2 inhibitor Nutlin as negative control. Lower panel, similar to above, but the immunoprecipitation was performed using biotin conjugated CTX1, presence of HDMX protein band indicates the direct binding of HDMX and CTX1.

Figure 5:
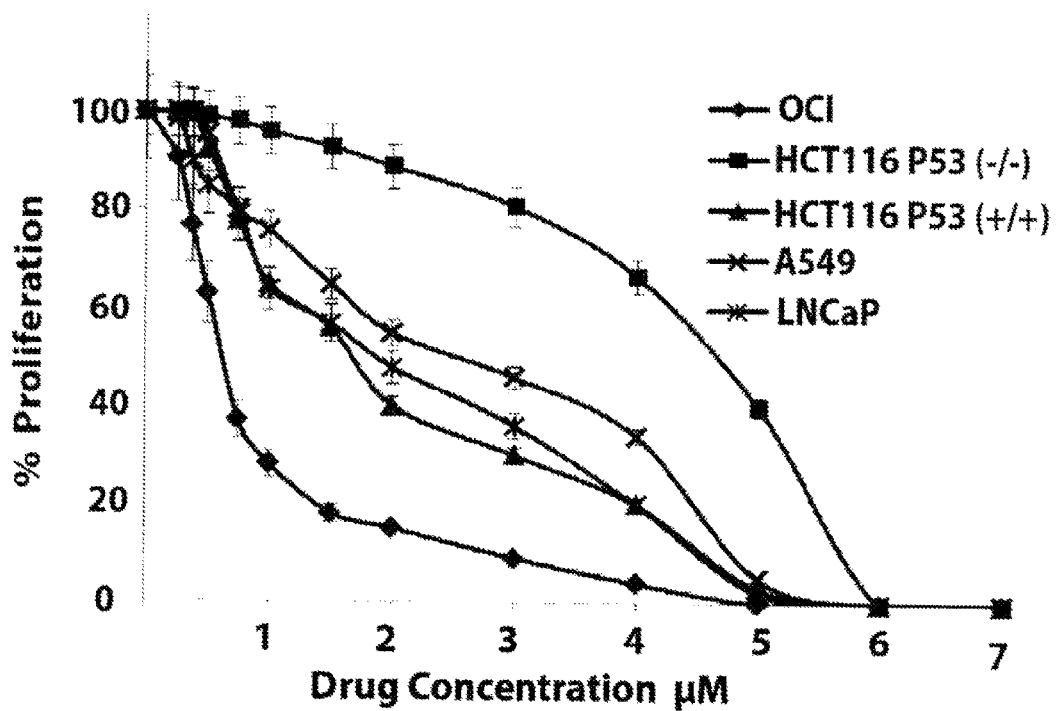

FIG. 5 shows that CTX1 preferentially impairs the growth of cells expressing wild-type p53. The indicated cells were treated with CTX1 and cell cycle analysis was performed using PI staining at 24 hr or proliferation was assessed using the MTT assay at 72 hr.

Figure 6:
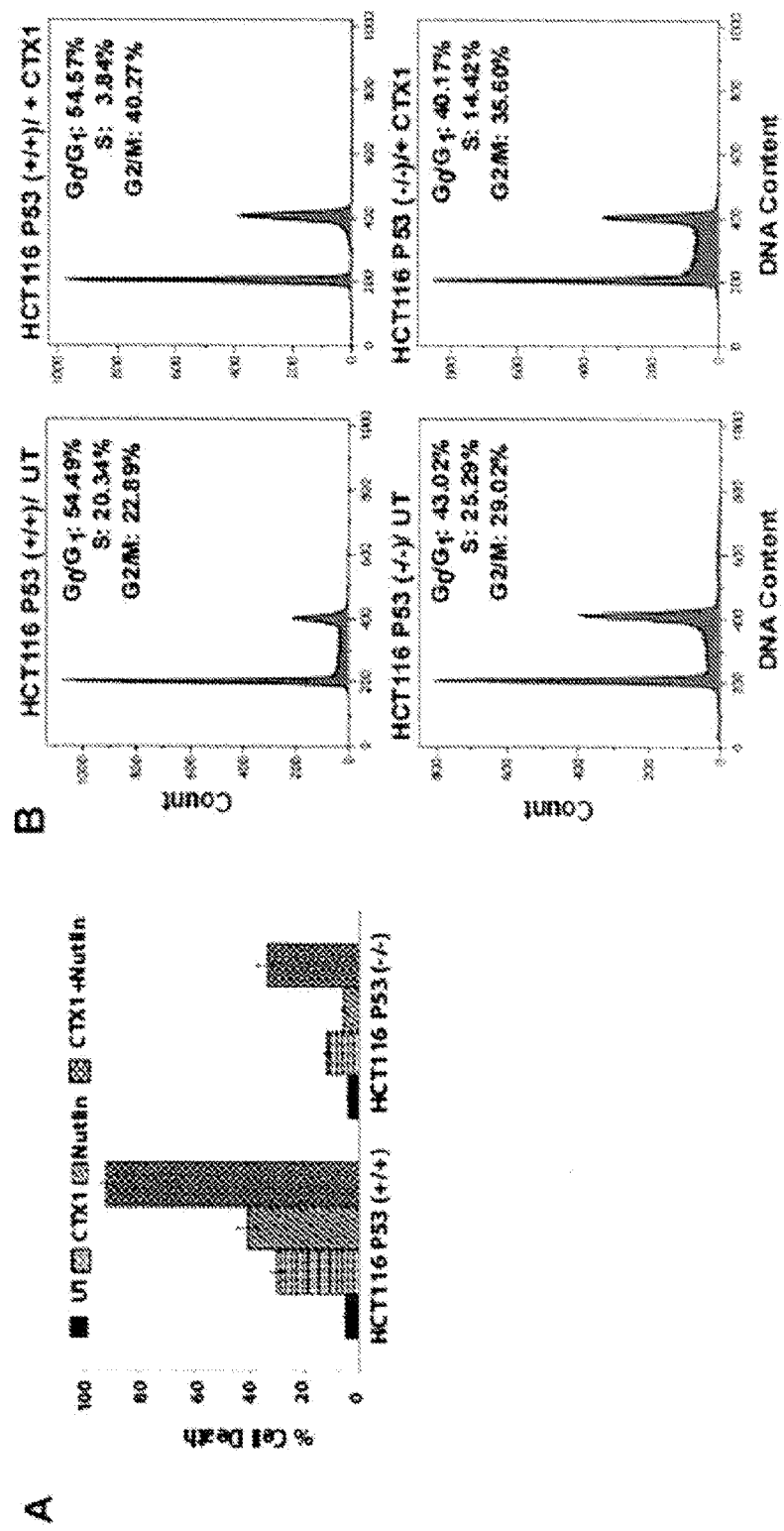

FIG. 6 shows that CTX1 preferentially impairs cancer growth expressing P53. A-B) CTX1 preferentially impairs the growth of cells expressing wild-type p53. HCT116 p53+1+ or p53-null cells were treated with CTX1 (2 μM) and cell cycle analysis was performed using PI staining at 24 hr.

Figure 7:
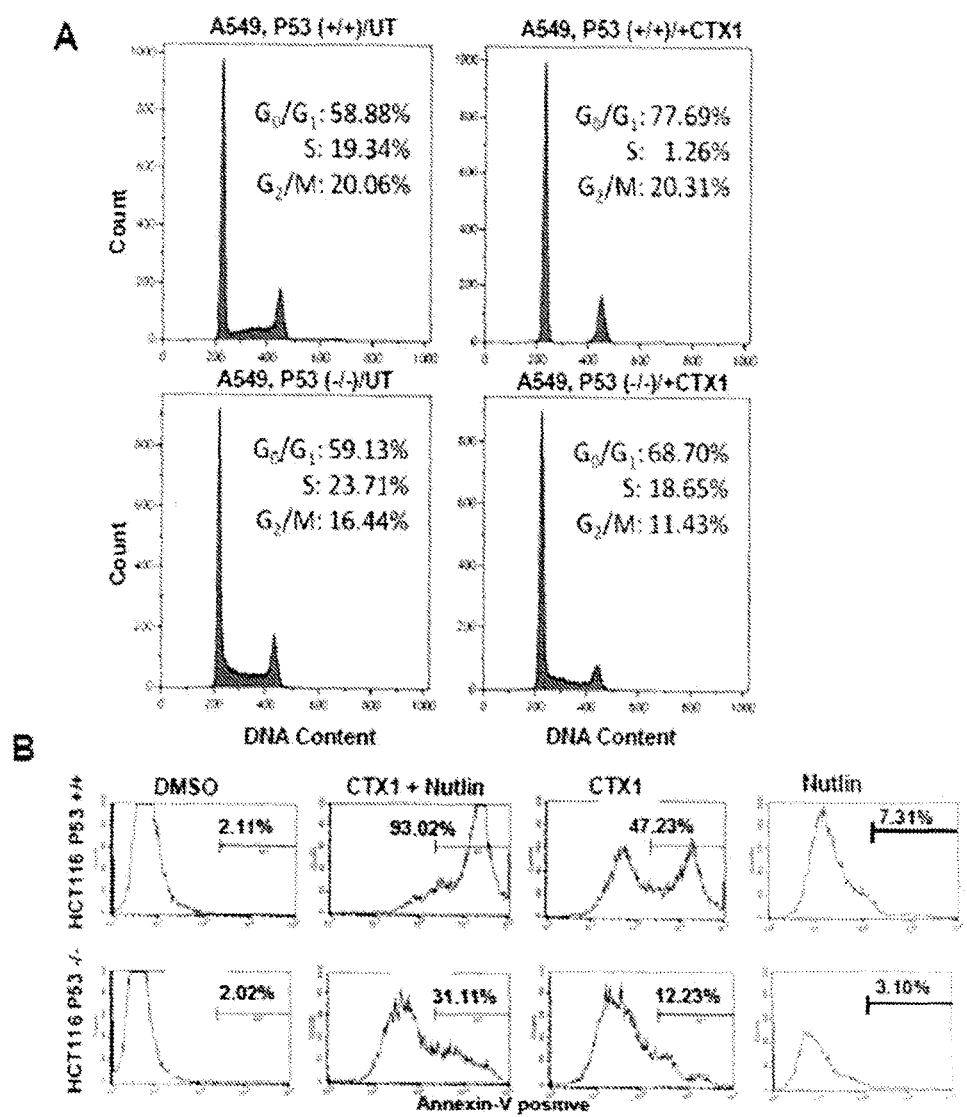

FIG. 7 shows that CTX1 can kill and inhibit the growth alone and in combination with nutlin 3 in cancer cells. A) preferentially impairs the growth of lung cancer cells expressing wild-type p53. A549 cells were treated with CTX1 (3 μM) and cell cycle analysis was performed using PI staining at 24 hr. B) The combination of CTX1 and nutlin-3 lead to significant apoptosis. The indicated cell lines were treated with CTX1 (3 μM), nutlin-3 (5 μM), or a combination for 72 hr and cell death was assessed by Annexin-V staining. C. CTX1 impairs the growth of a variety of cancer cells. The indicated cells were treated with the indicated doses of CTX1 and proliferation was assessed using the MTT assay at 72 hr.

Figure 8:
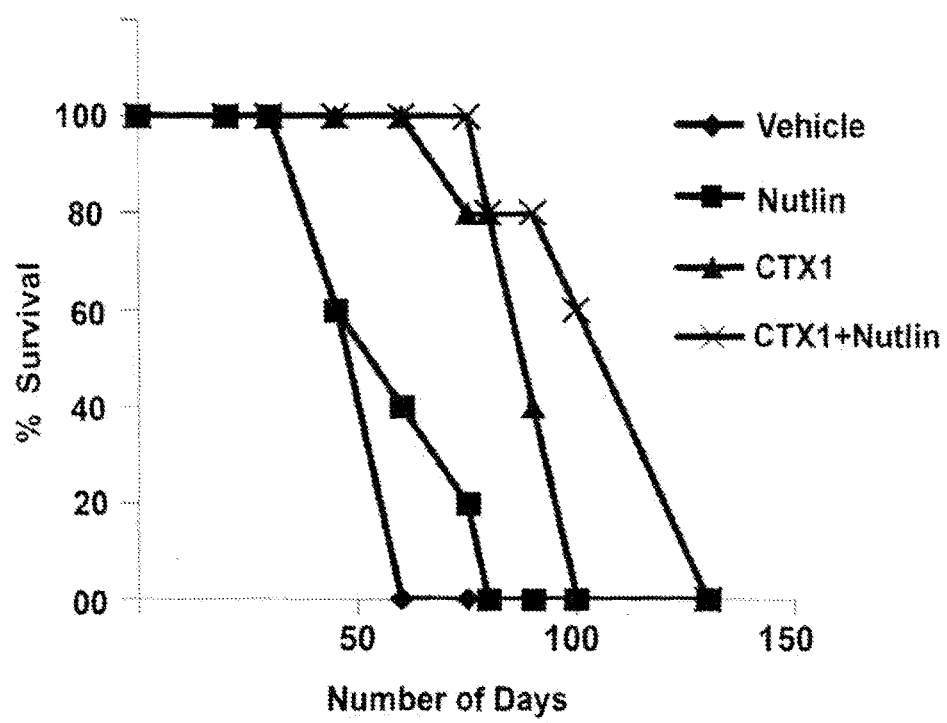

FIG. 8 shows that CTX1 demonstrates significant anticancer activity in vivo. NSG mice were injected with primary human AML cells by the tail vein (5×10⁶ cells in 100 μl of media) and mice were treated with CTX1 (30 mg/kg ip) or Nutlin-3 (200 mg/kg po) and assessed for survival.

DETAILED DESCRIPTION

The present invention provides for compounds, salts and derivatives thereof comprising the following:

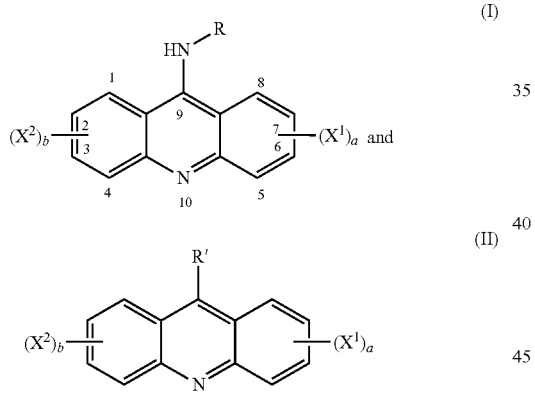

wherein each of $X^1$ and $X^2$ is individually selected from cyano, iodo, halogen, nitro, amide, phenyl, alkyl, cycloalkyl, aryl, heteroalkyl, heteroaryl, or alkoxy; 'a' and 'b' are individually 0 to 4; R is alkyl, alkenyl, alkynyl, cycloalkyl, aryl, sulfonyl, sulfate, indole, isatin, quinoline, indazole, aminobenzothiazole, phenylmorpholine, phenyl-pyrrole, aminophenylamine, propylsulfonylphenylamineazide, bromopropylsulfonylphenylamine, ethanol, chloroethylphenylamine, dichlorethylphenylamine, ethanolphenylamine, biotinphenylamine, methylsulfonylphenylamine, aminophenol, aminobenoic acid, bromophenylamine, dibromophenylamine, cyanophenylamine, methoxylphenylamine, aminopyridine, pyridine n-oxide, hydroxyphenylacetamide, phenylamide, chlorophenylacetamide, heteroaryl; R' is cyano, halogen, carboxyl acid, amine, azide, tetrazole, hydrazine, hydroxylamine, sulfinate, pyridyl-oxadiazole-thiol.

By way of example, the following representative example compounds can be synthesized by the present invention:

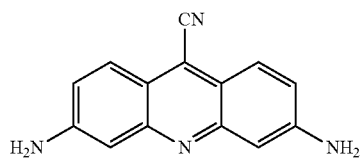
INVA3Z-2-1 (CTX-1)

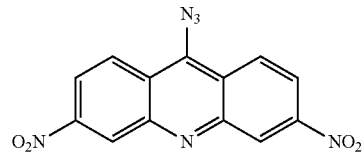
INVA3Z-55-2

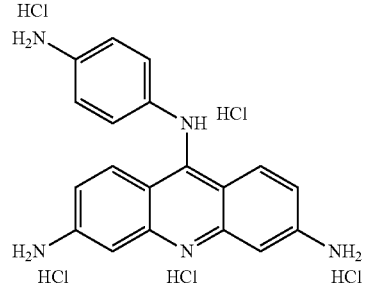
INVA3Z-56-1

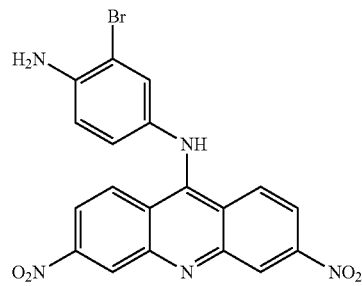
INVA3Z-53-2

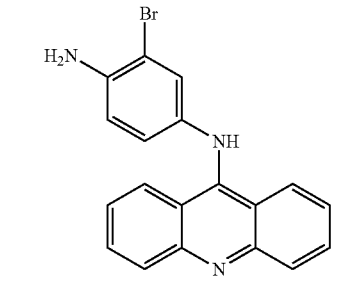
INVA3Z-54-2

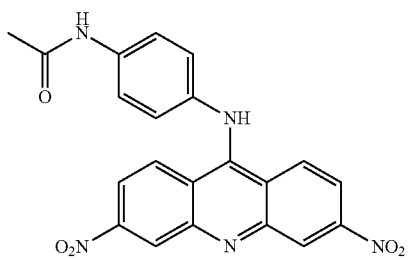
INVA3Z-50-1 (CTX-50)

-continued
INVA3Z-50-2
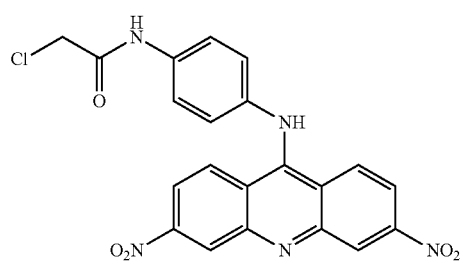
INVA3Z-52-3
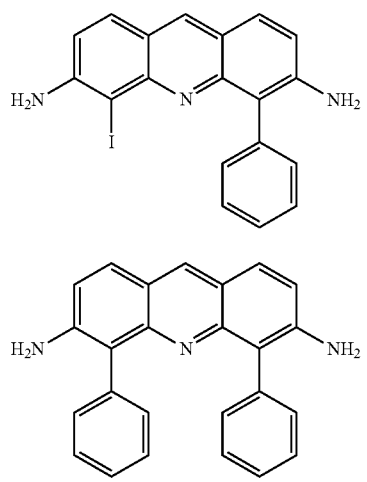
INVA3Z-52-2
INVA3Z-49-2
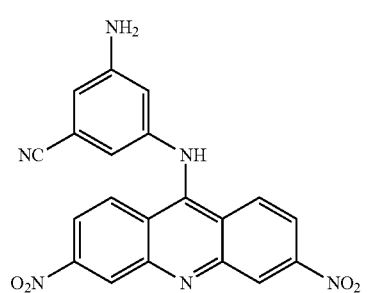
INVA3Z-49-1
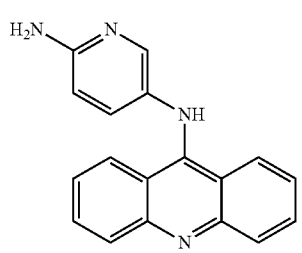
INVA3Z-58-1
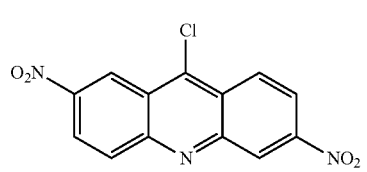
-continued
INVA3Z-59-2
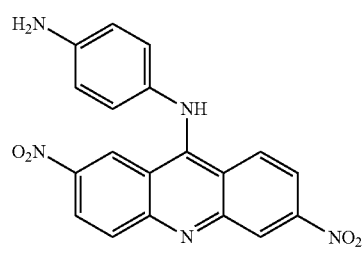
INVA3Z-60-3
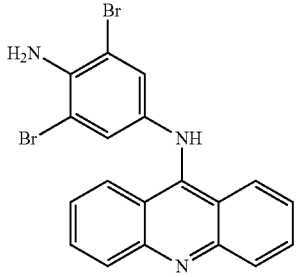
INVA3Z-61-1
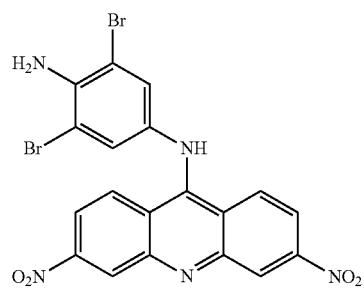
INVA3Z-58-2
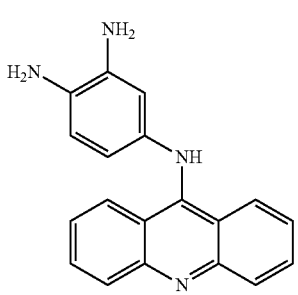
INVA3Z-61-2
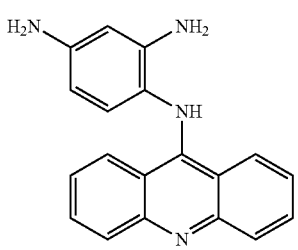

INVA3Z-62-1
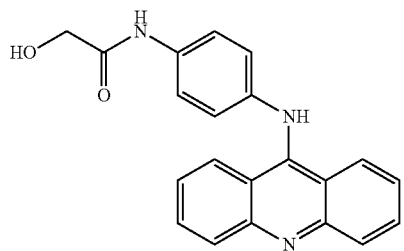
INVA3Z-62-2
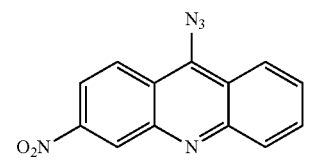
INVA3Z-63-1
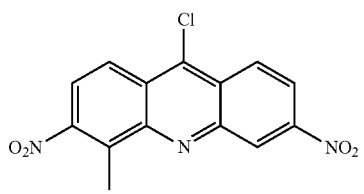
INVA3Z-63-2
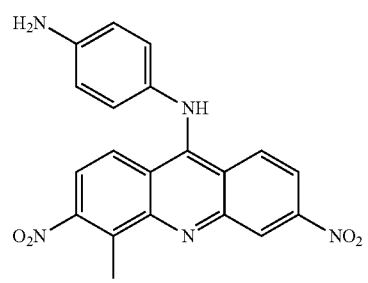
INVA3-64-1
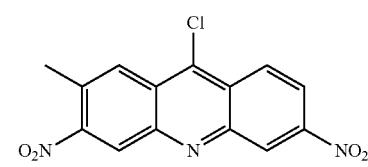
INV-A3-64-3
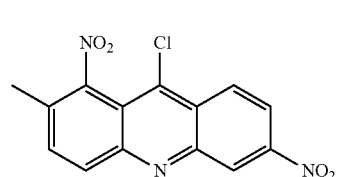
INV-A3-65-1
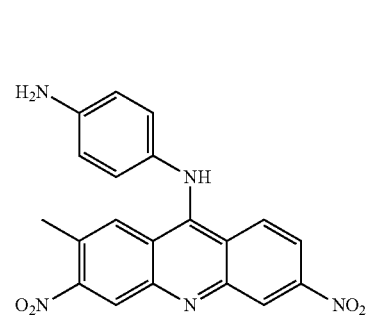
INVA3Z-65-2
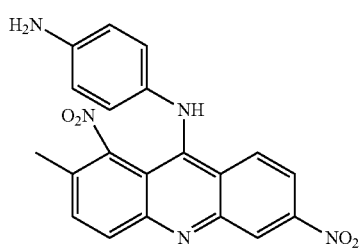
INVA3Z-66-1
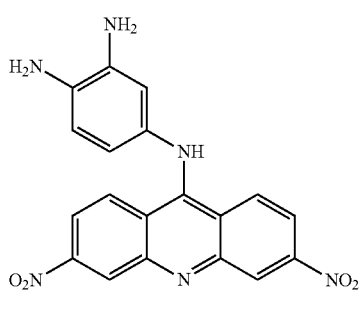
INVA3Z-66-2
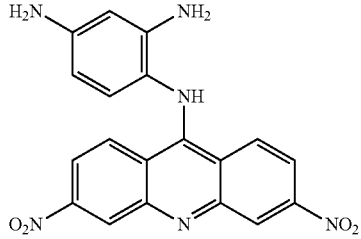
INVA3Z-67-1
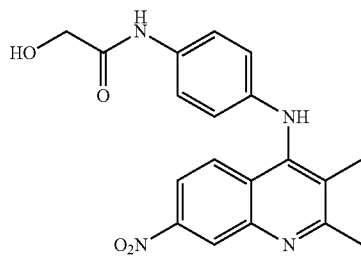
INVA3Z-68-1
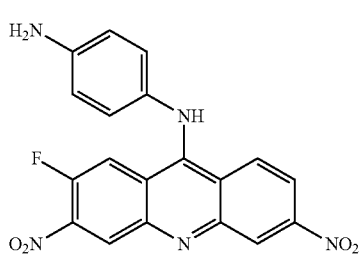
INVA3Z-68-2
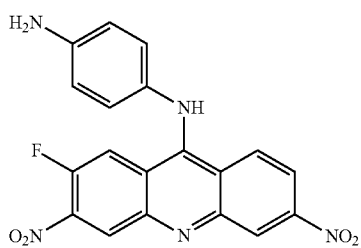

INVA3Z-69-2
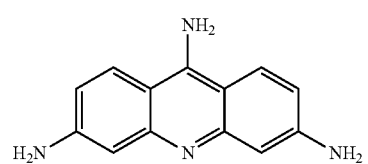
INVA3Z-70-2
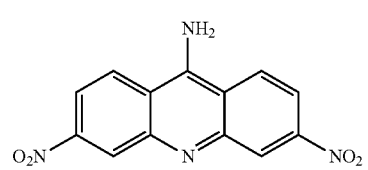
INVA3Z-71-1a
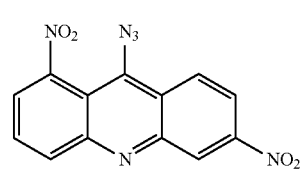
INVA3Z-66-3
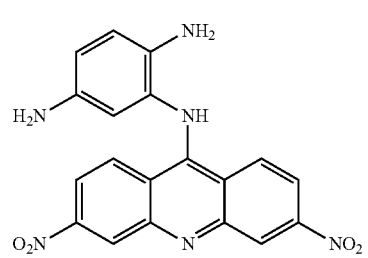
INVA3Z-72-1
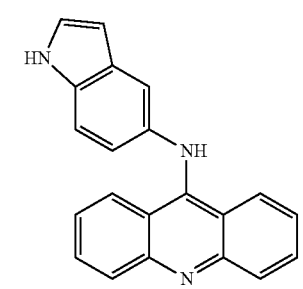
INVA3Z-72-2
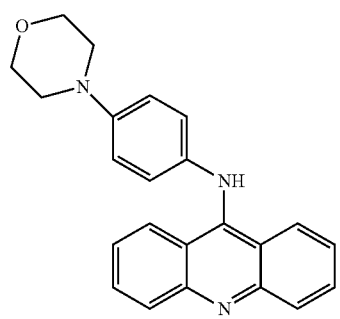
INVA3Z-73-1
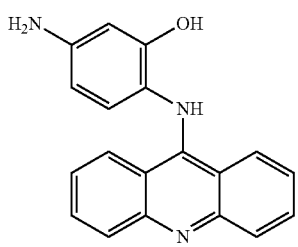
INVA3Z-75-1
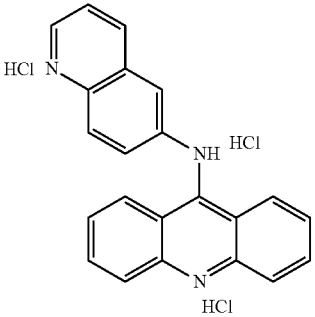
INVA3Z-75-2
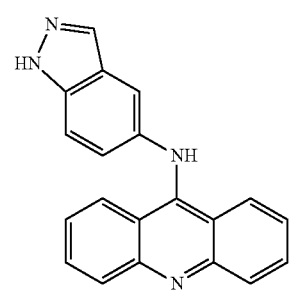
INVA3Z-76-2
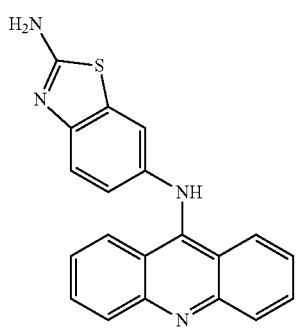
INVA3Z-77-1
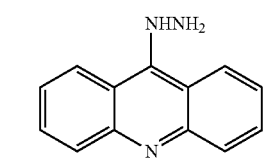
INVA3Z-77-2
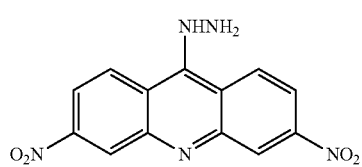

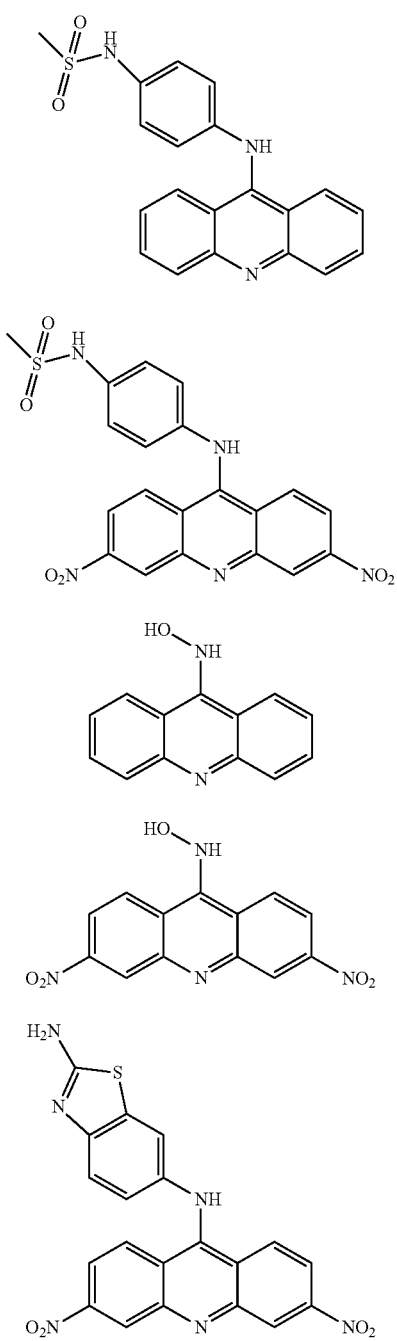
INVA3Z-78-1
INVA3Z-78-2
INVA3Z-80-1
INVA3Z-80-2
INVA3Z-81-2
INVA3Z-82-1
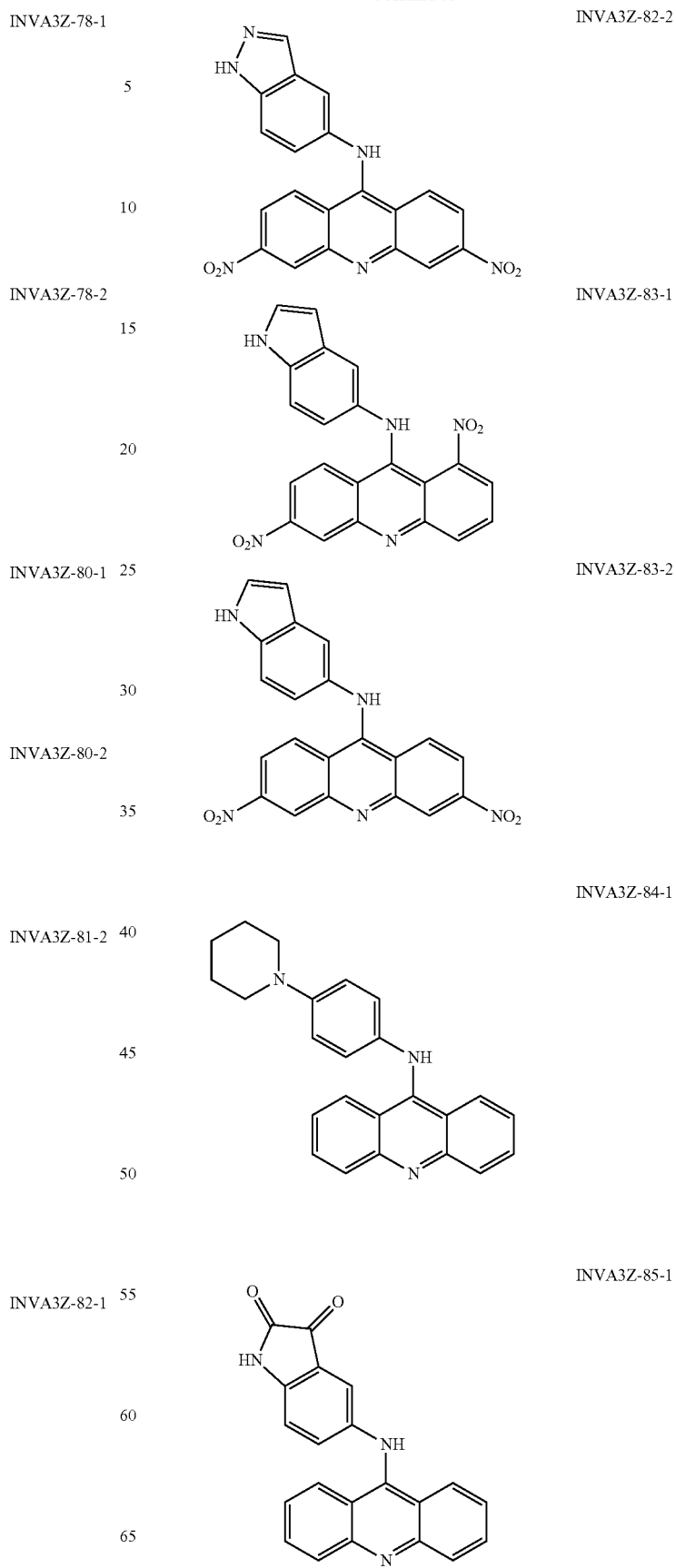
INVA3Z-82-2
INVA3Z-83-1
INVA3Z-83-2
INVA3Z-84-1
INVA3Z-85-1

INVA3Z-86-1
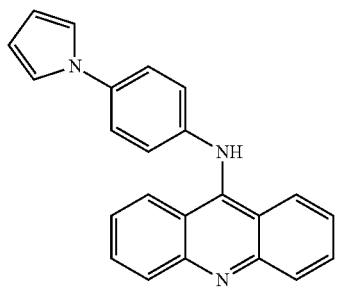
INVA3Z-84-3
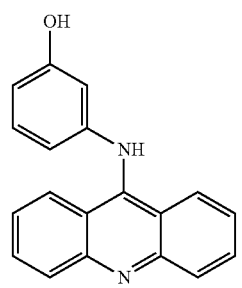
INVA3Z-86-2
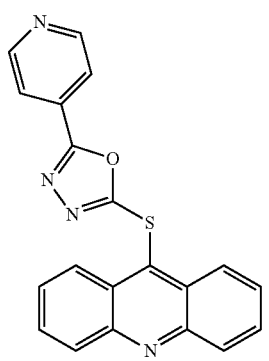
INVA3Z-88-1
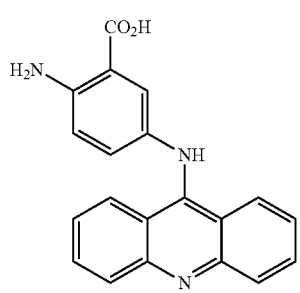
INVA3Z-88-2
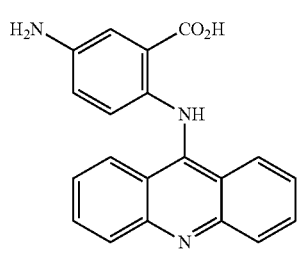
INVA3Z-89-1
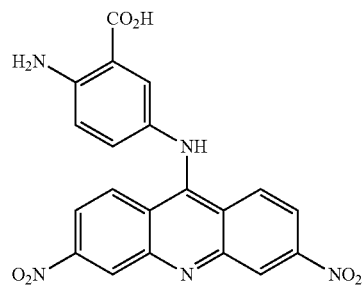
INVA3Z-89-2
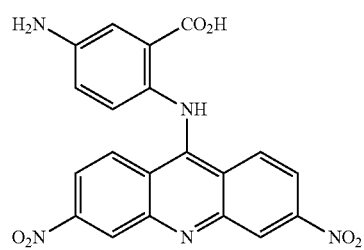
INVA3Z-91-2
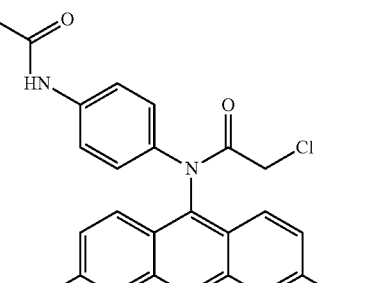
INVA3Z-92-1
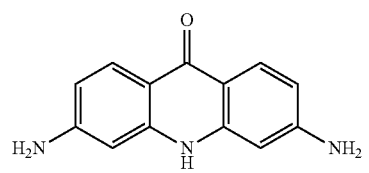
INVA3Z-94-1
INVA3Z-98-2
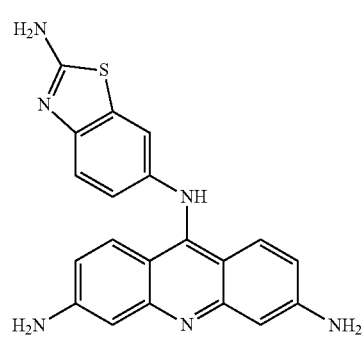

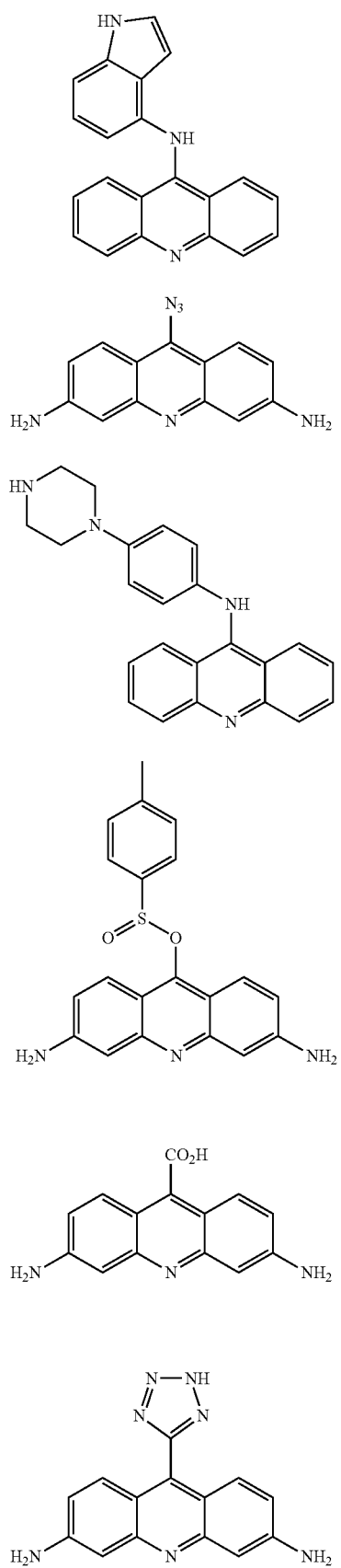

INVA3Z-1-1
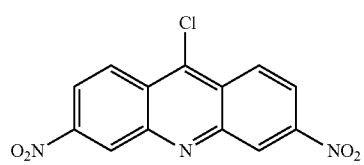
INVA3Z-6-1
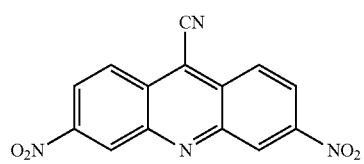
INVA3Z-6-3
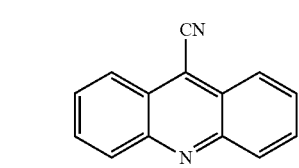
INVA3Z-10-1
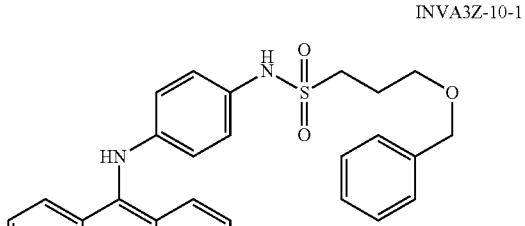
INVA3Z-13-1
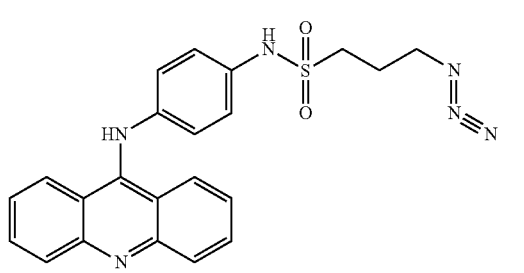
INVA3Z-14-1
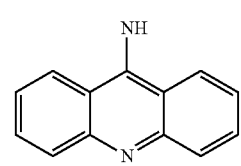
INVA3Z-17-2
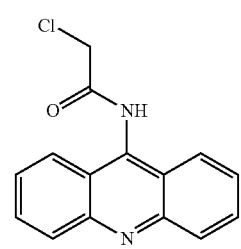
INVA3Z-5-2
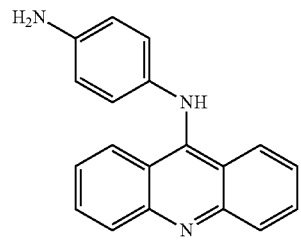
INVA3Z-19-1
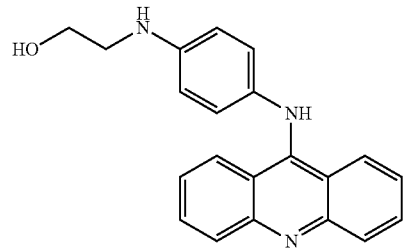
INVA3Z-21-2
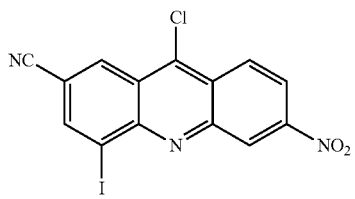
INVA3Z-23-2
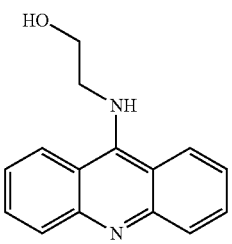
INVA3-24-2
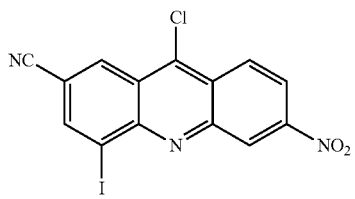
INVA3Z-26-3
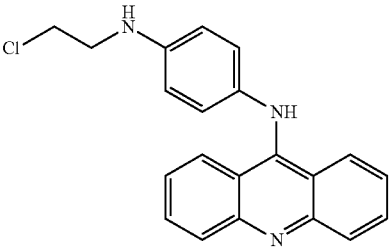

INVA3Z-28-1

INVA3Z-29-1

INVA3Z-29-2

INVA3Z-30-1

INVA3Z-30-3

INVA3Z-31-1

INVA3Z-32-1

INVA3Z-32-2

INVA3Z-36-1

INVA3Z-37-1

INVA3Z-38-1

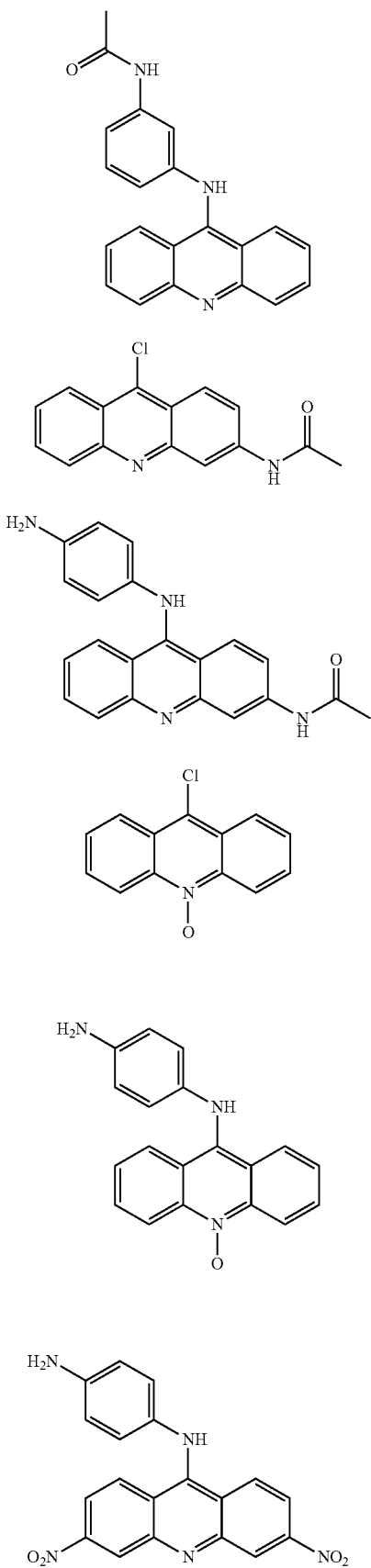
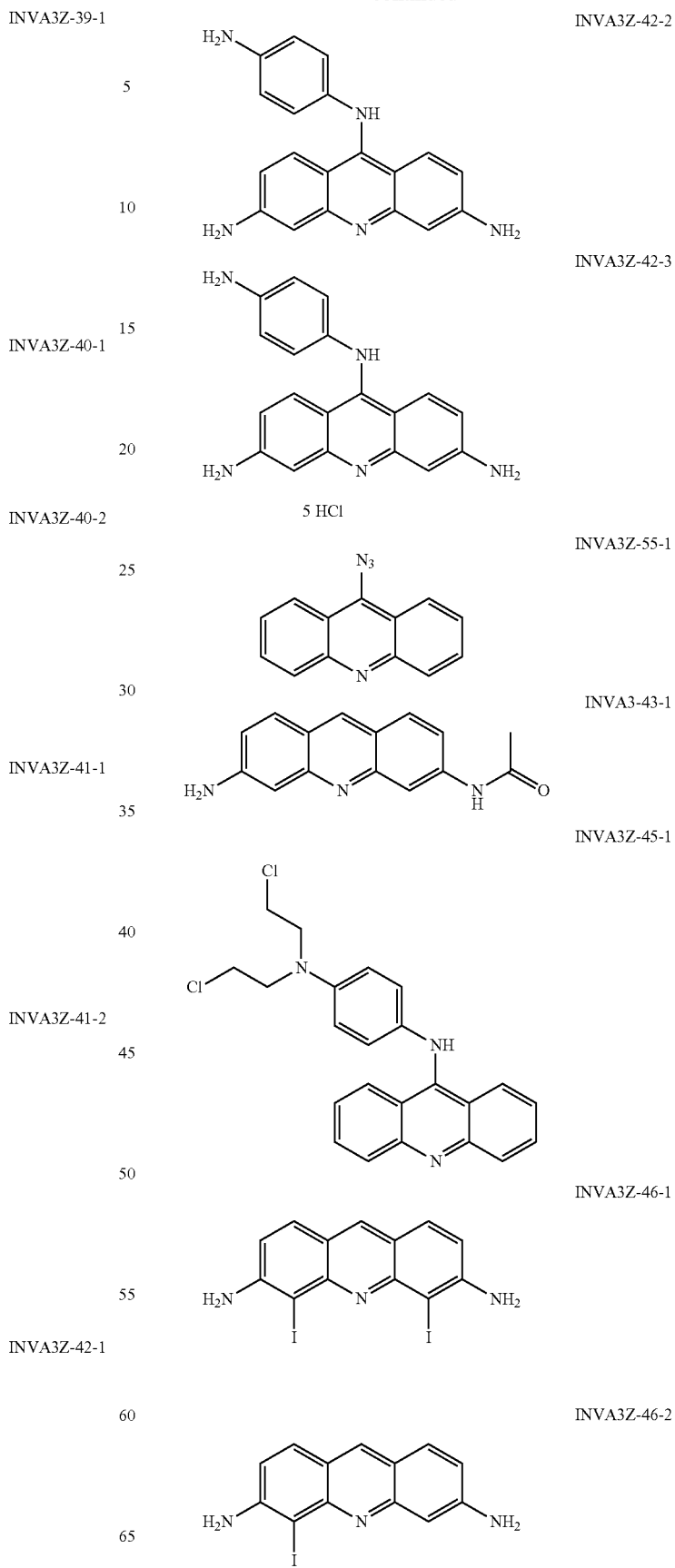

-continued

INVA3Z-47-2

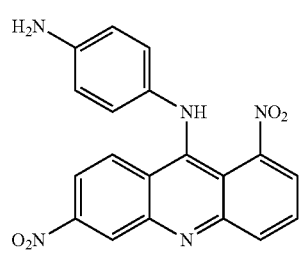

INVA3Z-48-2

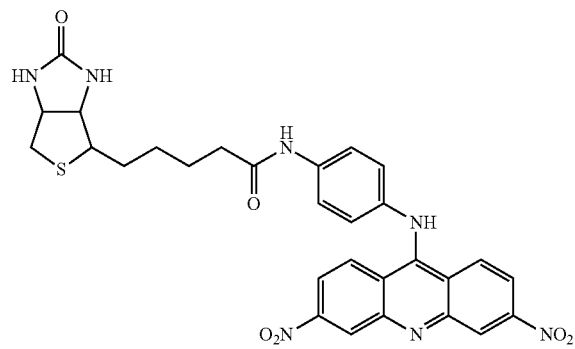

The compounds of the present invention can be prepared generally by mixing compound A (see, Albert, J. Chem. Soc. 1936, p 88-93) with 1,4-phenylenediamine and potassium carbonate in DMF as follows (method A):

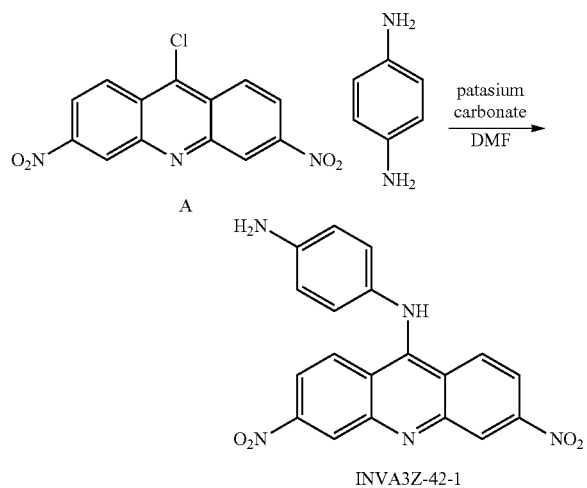

Alternatively, compound B (see Moehrle, Scientia pharmaceutica, 1997, vol. 65, #1-2 p. 11-20) can be mixed with benzeneboronic acid and bis(triphenylphosphine) palladium (II) dichloride and potassium carbonate with water in THF, as follows (method B):

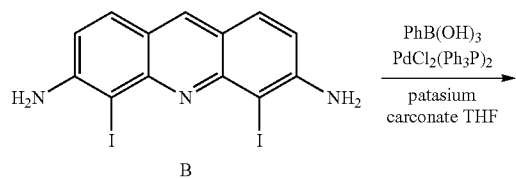

-continued

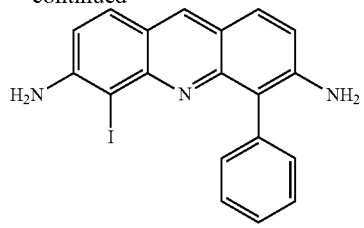

INVA3Z-51-3

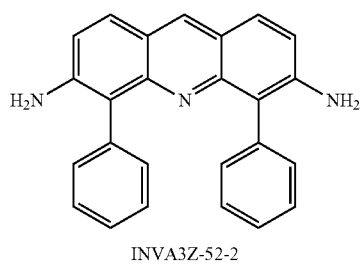

INVA3Z-52-2

All acridine compounds described herein can be prepared in a HCl salt form following treatment with 0.5 M HCl MeOH. Acridine phenyl amides can be prepared following method A using aminophenyl amide instead of diaminobenzene. Biotin conjugates (such as INVA3Z-31-1, INVA3Z-48-2) can be prepared from parent acridine compounds with DCC coupling in DMF, DMAP and HOBt as catalysts. Chloroacridine N-oxide derivatives can be prepared by adding peracetic acid in DCM. Aminophenyl acridine N-oxide derivatives can be prepared by utilizing chloroacridine N-oxide in method A. Amine, hydrazine, hydroxylamine acridine derivatives can be prepared following method A, and azide acridine derivatives can further be prepared following method A without KOH. Substituted chloroacridine derivatives can be prepared adapting the reactions described by Albert (J. Chem. Soc. 1936, p 88-93) and acridones can be adapting the reactions described by Moore (J. B. J. Med. Chem. 2006, 49, p 582-599).

The compounds of the present invention induce p53 activity to varying degrees when administered to a variety of different cancer cell lines. Two representative compounds, CTX1 and CTX50, have been examined in depth to determine the mechanism of action for triggering cell death by the compounds of the present invention, as well as sites of protein-drug interaction and antitumor activity:

The compounds of the present invention have demonstrated the ability to induce p53 activity within a cell. As detailed in the examples below, the mechanism of action does not rely on prior or induced DNA damage. Analysis of cells with the compounds of the present invention demonstrated that the compounds do not induce measurable DNA damage at doses in which p53 induction was observed (see, FIGS. 1A-B).

The compounds of the present invention affect the interaction between HDMX and p53 to induce p53 activity. Targeting HDMX allows for harnessing p53 activity to induce apoptosis of a cell. This mechanism is particularly beneficial as HDM2 inhibitors such as Nutlin-3 do not show efficacy on cancer cells that overexpress HDMX. As set forth in the examples, the compounds of the present invention were examined in cells in which p53 was suppressed by HDMX or HDM2 overexpression, as well cells in which p53 expression was knocked down. The compounds of the present invention induced significant p53-dependent cell death in HDMX-expressing cells (transfected with vector or HDMX), but not cells in which p53 is inactivated by HDM2 overexpression or when p53 is knocked down using p53 targeting shRNA (FIG. 2A), thus demonstrating specificity in targeting HDMX. These data were confirmed in other cell models where HDMX is overexpressed, a opposite effect also observed when Nutlin3 was used independently (see FIGS. 2B and 2C).

The compounds of the present invention directly bind to HDMX as evidenced by biotin-conjugation, as well as with an observed spectral shift and various immunoprecipitation reaction (see FIG. 3). The interaction was further demonstrated using surface plasmon resonance (SPR), where HDMX demonstrated strong binding to the compounds of the present invention but not nutlin-3 (FIG. 4C). The ability to directly impair the interaction of p53 and HDMX then results in stabilization of p53 protein within a cell. Further, as set forth in the examples, the compounds of the present invention demonstrated specificity for binding to HDMX, as opposed to HDM2 (as shown in the various treatment combinations in cell culture studies).

The compounds of the present invention accordingly affect cancer cell growth and survival. As demonstrated in the examples, contacting the compounds of the present invention with cancer cells associated with irregular p53 activity exhibited growth inhibition and killing preferentially on wild type p53 expressing cells. Further, when combined with other p53 targeting molecules, such as the HDM2 inhibitor nutlin-3, synergistic or additive killing was observed.

The compounds of the present invention can exert their activity by arresting cell growth and inducing apoptosis. The cell can be in vitro, ex vivo or in vivo. As described herein, administering the compounds of the present invention to a cancer cell in vitro or in vivo to a subject with aberrant p53 activity resulted in reduced cancer cell growth and increased death/apoptosis of cancerous cells. The highly aggressive AML model system that closely mimics human disease (using a primary human AML sample derived from a patient with refractory and relapsed AML), demonstrated that the compounds of the present invention, even as single agents, significantly enhanced the survival rate in this model system (FIG. 8). Of particular importance with the model system utilized is that no other existing therapeutic is efficacious in such a patient population.

The present invention also provides methods of treating a cell comprising administering to a cell the compounds described herein. The cell may be in vitro, in vivo or ex vivo. The cell may be within a subject, such as an animal. The subject may be a human. The cell may be predetermined to have irregular p53 activity or HDMX activity. The cell may be selected based on aberrant p53 activity, or on HDMX activity. The cell may be selected based on increased expression of HDMX or p53.

The compounds of the present invention may be administered to a cell by traditional routes of administration. For cells in vitro, the compounds can be administered to a surrounding media that is in contact with the cells. For cells within a subject, the compounds may be administered by injection or by oral administration, inhalation or as a suppository.

The compounds of the present invention may be administered to a cell in an effective amount. As described herein, efficacy of the compounds of the present invention can be readily determined based on the observable binding to HDMX, the changes in p53 activity and in the changes to cell survival/death/apoptosis. The compounds of the present invention may also be optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution.

The compounds of the present invention may be administered with a further therapeutic agent. As described herein, administration with nutlin-3 resulted in superior cancer cell death/apoptosis. Those skilled in the art will appreciate that further chemotherapeutic agents can also be included in a treatment regimen (such as those listed at www.cancer.gov/cancertopics/treatment/drugs). Those skilled in the art will also appreciate that the compounds of the present invention can be added to existing therapies, particularly those associated with p53 activity or reduced cell apoptosis.

EXAMPLES

Preparation of compounds:
Method A:
A mixture of compound A (Ref. Albert; Linnell J. Chem. Soc. 1936, p 88, 93) (30 mg, 0.1 mmol), 1,4-phenylenediamine (11 mg, 0.1 mmol) and potassium carbonate (28 mg, 0.2 mmol) in DMF (2 ml) solution was stirred at 50° C. for 1 h. EtOAc (15 ml) and water (15 ml) was added into the mixture to quench the reaction, the aqueous layer was removed, and the organic layer was washed again with water (10×2 ml). The EtOAc solvent was evaporated, and the residue was subjected to silica gel column chromatography (EtOAc: Hexanes) to furnish INVA3Z-42-1 (20 mg, yield 53%).

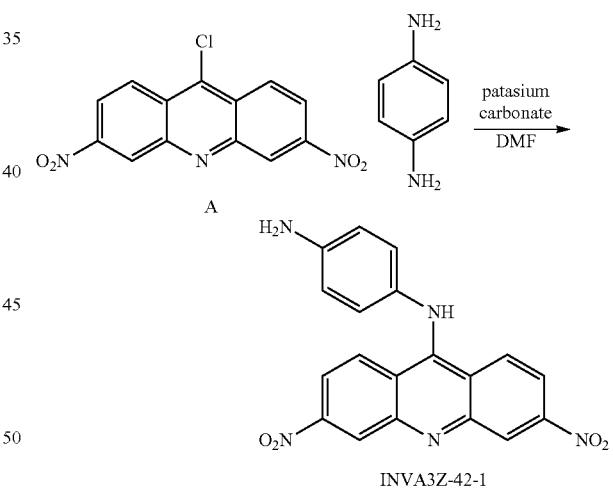

Method B:
A mixture of compound B (Ref. Moehrle; Von Der Lieck-Waldheim Scientia pharmaceutica, 1997, vol.65, #1-2 p. 11-20) (34 mg, 0.1 mmol), benzeneboronic add (24 mg, 0.2 mmol), bis(triphenylphosphine) palladium(II) dichloride (7 mg, 0.01 mmol), potassium carbonate (28 mg, 0.2 mmol) and water (100 ul) in THF (5 ml) solution was refluxed at 120° C. for 30 min. The reaction mixture was cooled down to room temperature and diluted with EtOAc (30 ml). The mixture was washed with water (20×3 ml); the organic solvent was evaporated, and the residue was applied to a silica gel column (EtOAc:Hexanes:MeOH) to give INVA3Z-52-3 (15 mg, yield 37%), and INVA3Z-52-2 (8 mg, yield 22%).

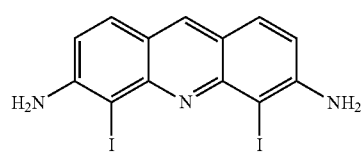

B

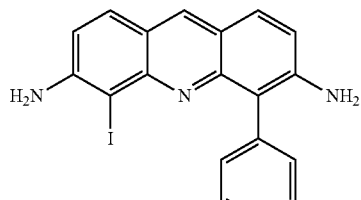

INVA3Z-51-3

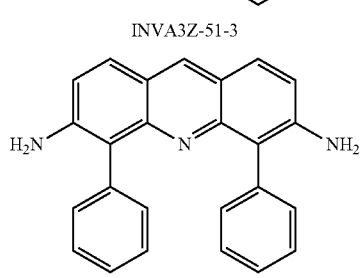

INVA3Z-52-2

For further synthesis of the particular compounds, all acridines can be prepared in HCl salt form when they are treated with 0.5 M HCl MeOH. Acridine phenyl amides can be prepared using method A using aminophenyl amide instead of diaminobenzene. Biotin conjugates (INVA3Z-31-1, INVA3Z-48-2) were prepared from the parent acridine compounds with DCC coupling in DMF, DMAP and HOBt as catalysts. Chloroacridine N-oxide was prepared by peracetic acid in DCM; aminophenyl acridine N-oxide was prepared from chloroacridine N-oxide in method A. Amine, hydrazine, hydroxylamine acridine derivatives were prepared in method A, and azide acridine was also prepared in method A without KOH. Substituted chloroacridine was prepared in the same way as described in the reference (Albert; Linnell J. Chem. Soc. 1936, p 88, 93). Acridones were prepared according to the reference (Moore; Michael J. B. J. Med. Chem. 2006, 49, p 582, 599).

Based on these steps, the following compounds have been synthesized:

INVA3Z-2-1 (CTX-1)

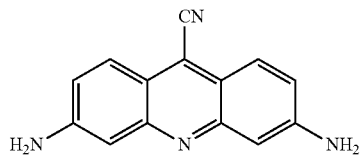

INVA3Z-55-2

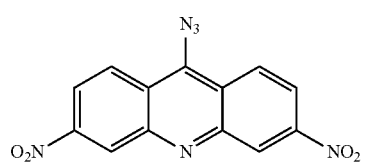

INVA3Z-56-1

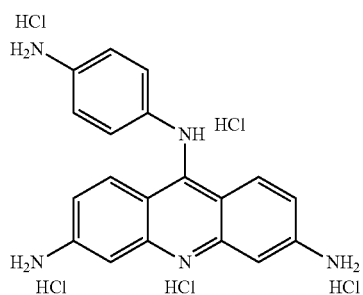

INVA3Z-53-2

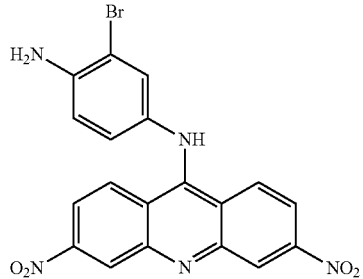

INVA3Z-54-2

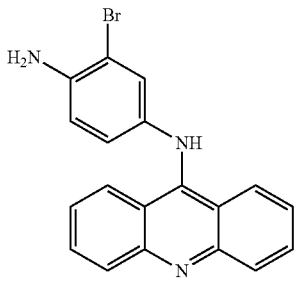

INVA3Z-50-1 (CTX-50)

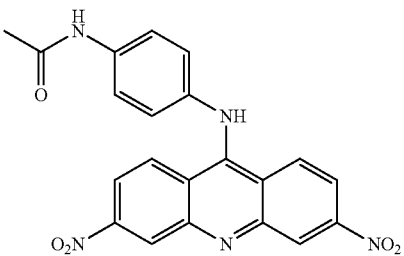 [SMILES: CC(=O)Nc1ccc(Nc2c3ccc([N+](=O)[O-])cc3nc3cc([N+](=O)[O-])ccc23)cc1]

INVA3Z-50-2

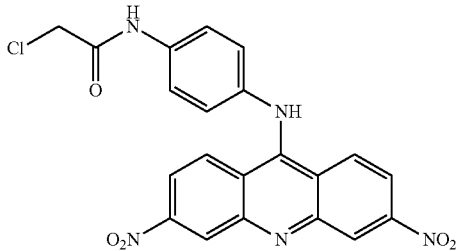

INVA3Z-52-3
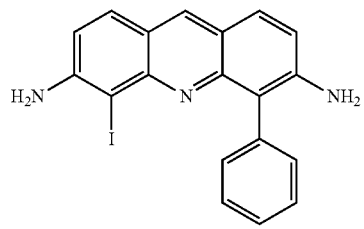
INVA3Z-52-2
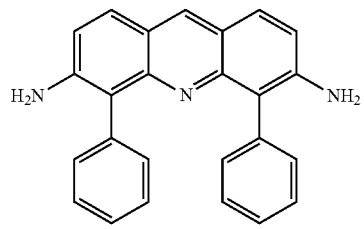
INVA3Z-49-2
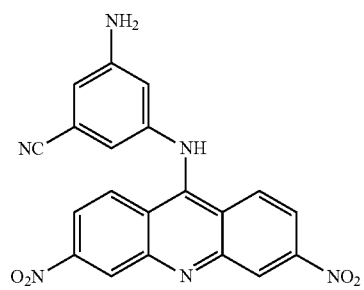
INVA3Z-49-1
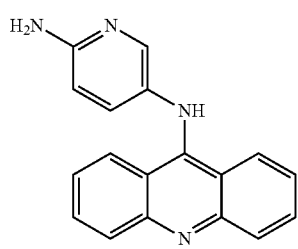
INVA3Z-58-1
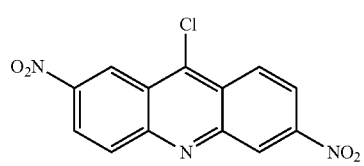
INVA3Z-59-2
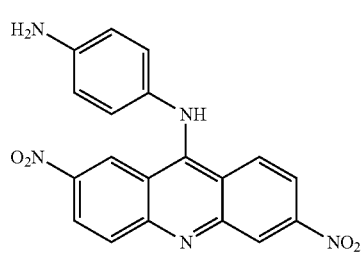
INVA3Z-60-3
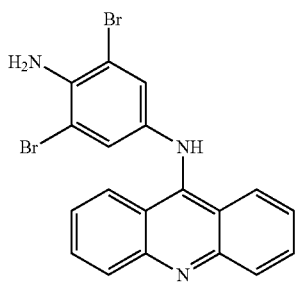
INVA3Z-61-1
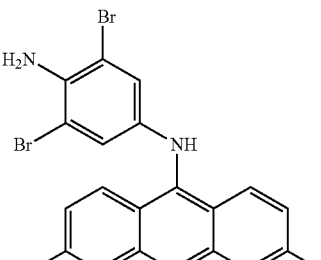
INVA3Z-58-2
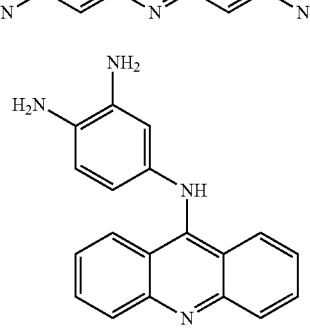
INVA3Z-61-2
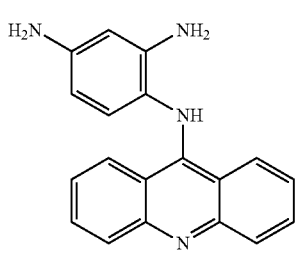
INVA3Z-62-1
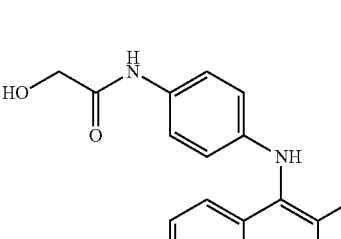
INVA3Z-62-2
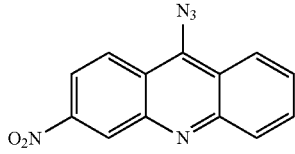

INVA3Z-63-1
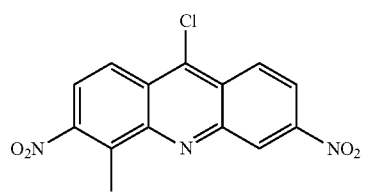
INVA3Z-63-2
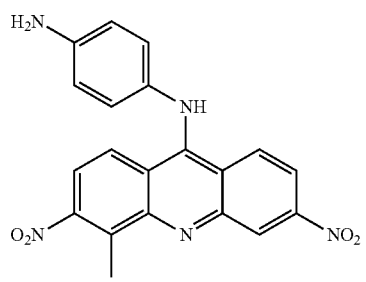
INVA3-64-1
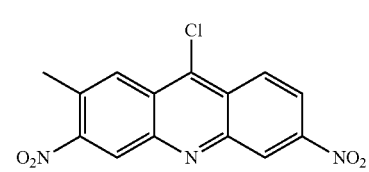
INV-A3-64-3
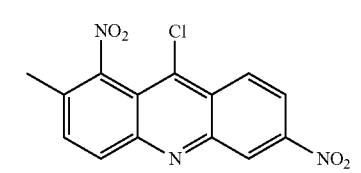
INV-A3-65-1
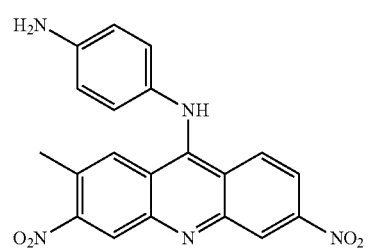
INVA3Z-65-2
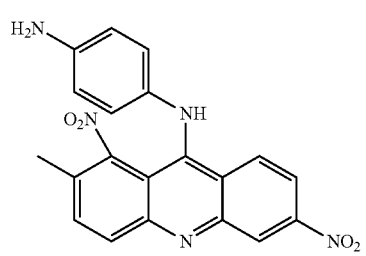
INVA3Z-66-1
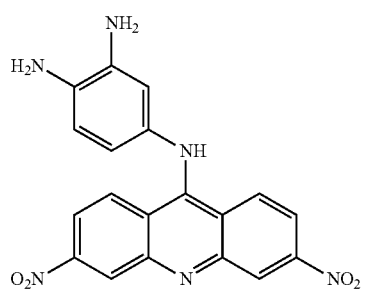
INVA3Z-66-2
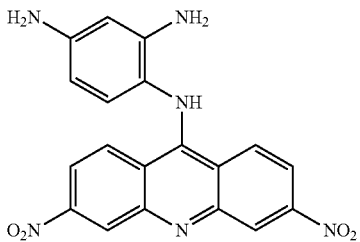
INVA3Z-67-1
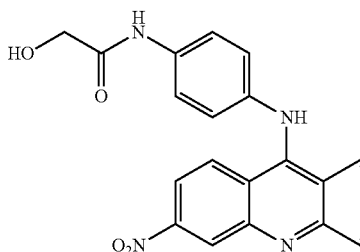
INVA3Z-68-1
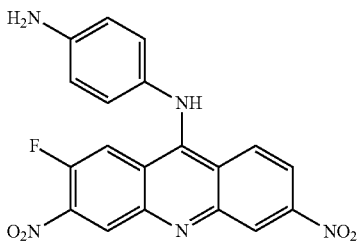
INVA3Z-68-2
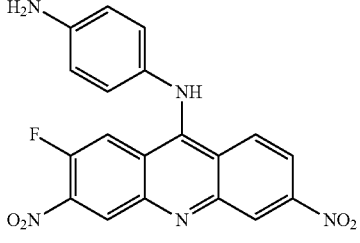
INVA3Z-69-2
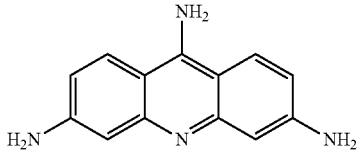
INVA3Z-70-2
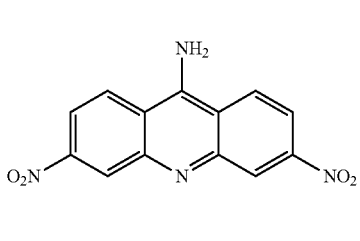
INVA3Z-71-1a
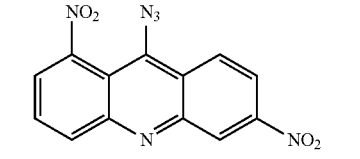

-continued
INVA3Z-66-3
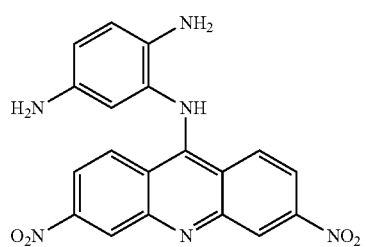
INVA3Z-72-1
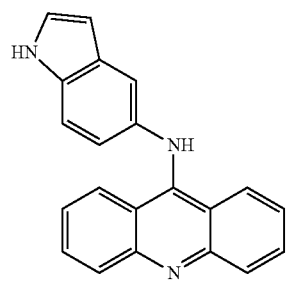
INVA3Z-72-2
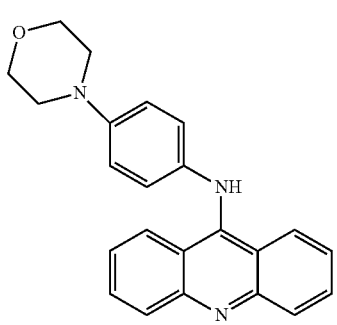
INVA3Z-73-1
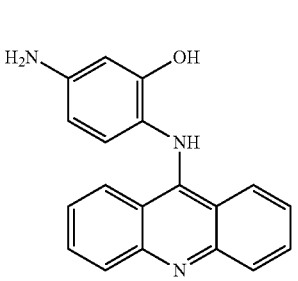
INVA3Z-75-1
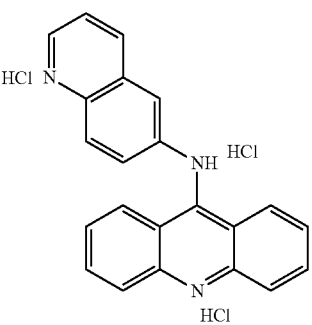
-continued
INVA3Z-75-2
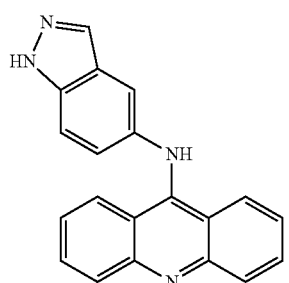
INVA3Z-76-2
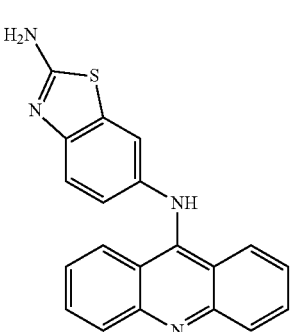
INVA3Z-77-1
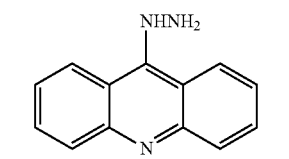
INVA3Z-77-2
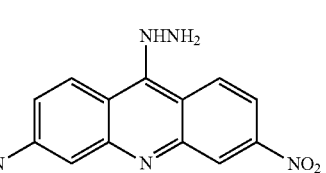
INVA3Z-78-1
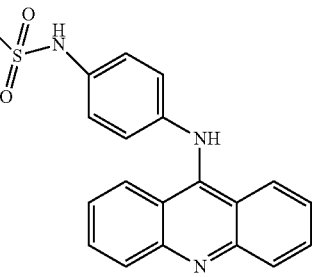
INVA3Z-78-2
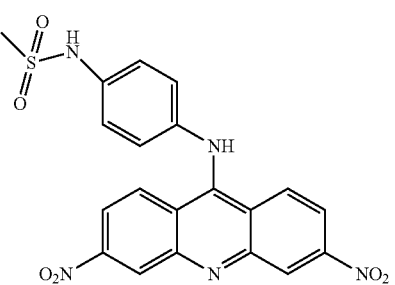

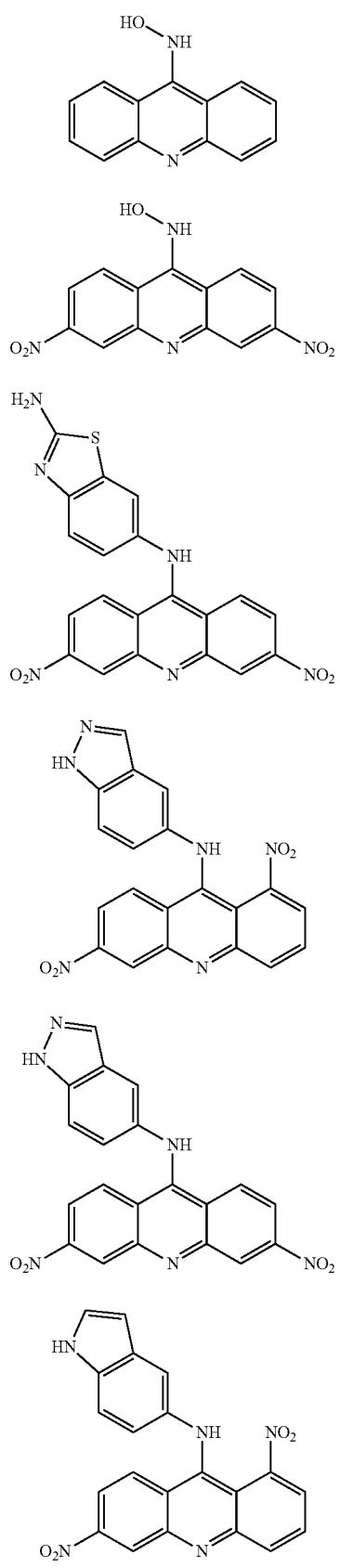
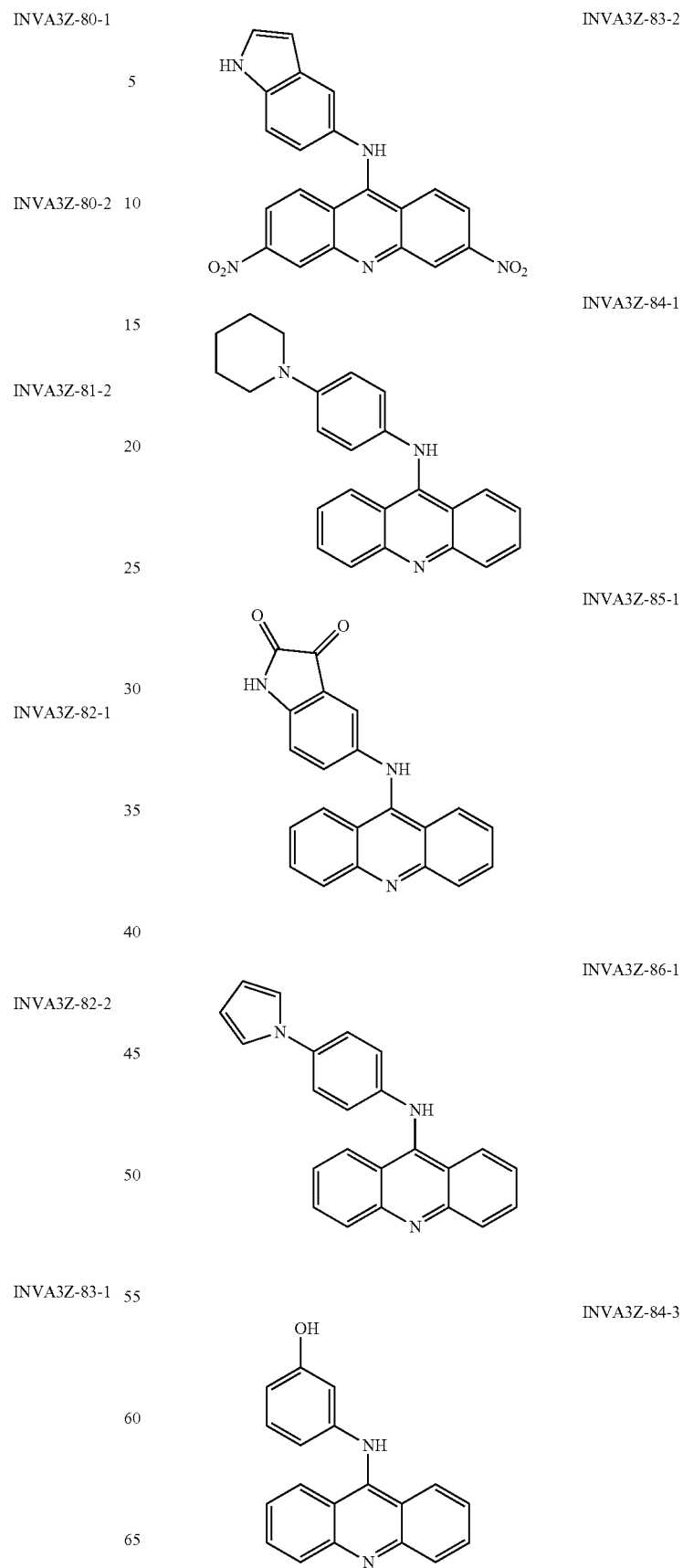

-continued

INVA3Z-86-2

INVA3Z-88-1

INVA3Z-88-2

INVA3Z-89-1

INVA3Z-89-2

-continued

INVA3Z-91-2

INVA3Z-92-1

INVA3Z-94-1

INVA3Z-98-2

INVA3Z-99-1

INVA3Z-100-1

INVA3Z-101-1
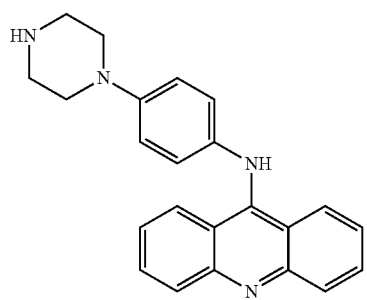
INVA3-103-1
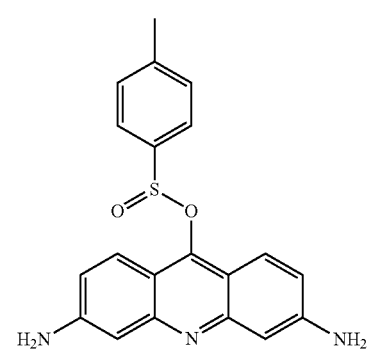
INVA3Z-104-1
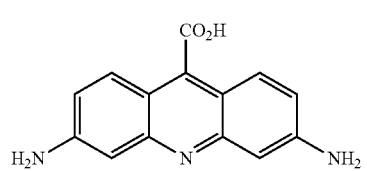
INVA3Z-107-1
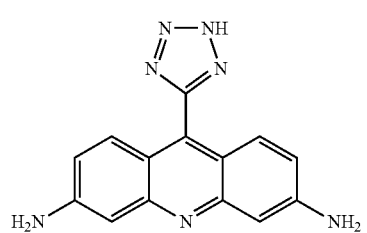
INVA3Z-108-1
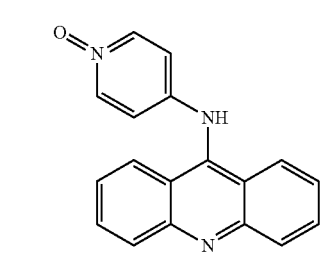
INVA3Z-109-1
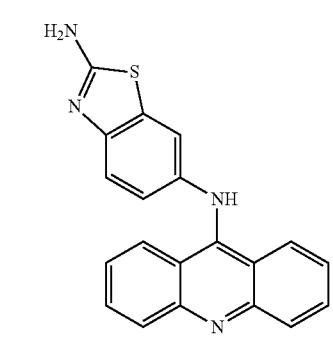
INVA3Z-110-1
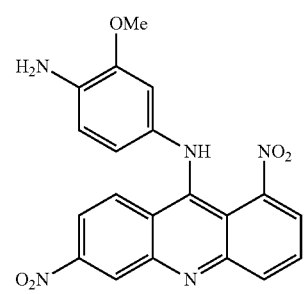
INVA3Z-110-2
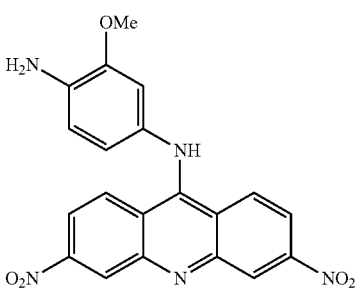
INVA3Z-111-1
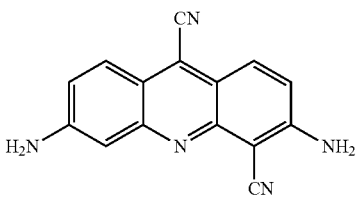
INVA3Z-112-1
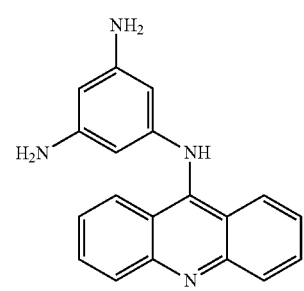
INVA3Z-1-1
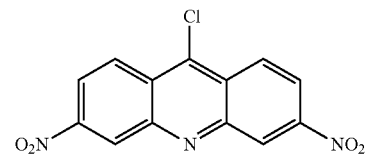
INVA3Z-6-1
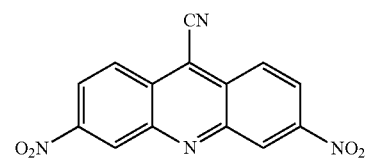
INVA3Z-6-3
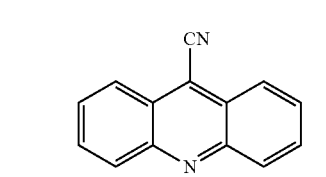

INVA3Z-10-1
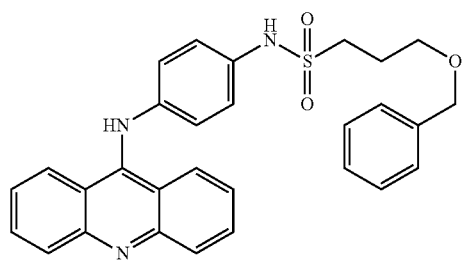
INVA3Z-13-1
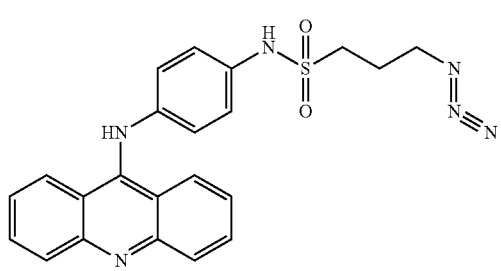
INVA3Z-14-1
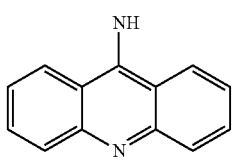
INVA3Z-17-2
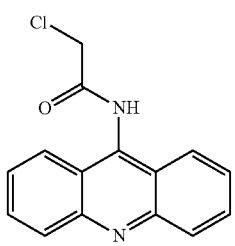
INVA3Z-5-2
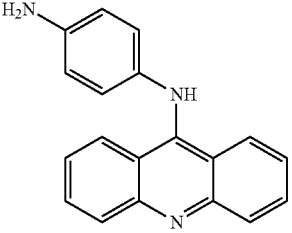
INVA3Z-19-1
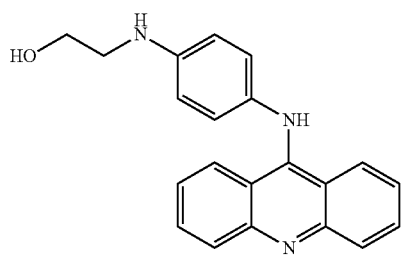
INVA3Z-21-2
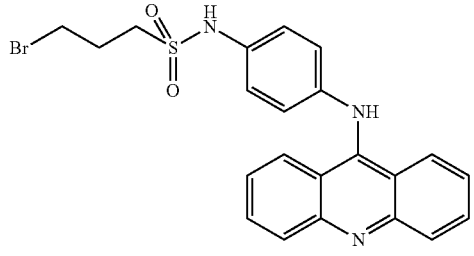
INVA3Z-23-2
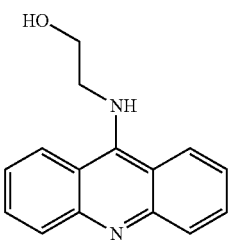
INVA3-24-2
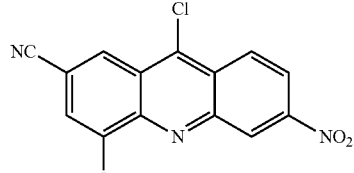
INVA3Z-26-3
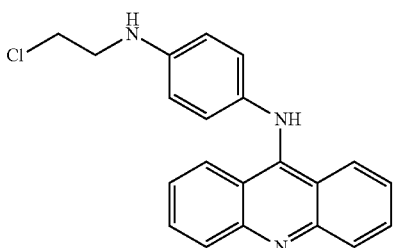
INVA3Z-28-1
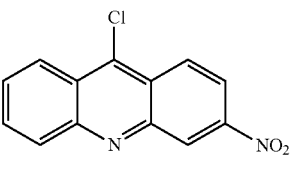
INVA3Z-29-1
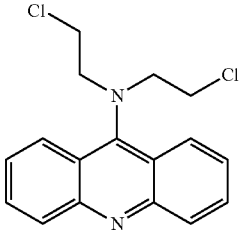
INVA3Z-29-2
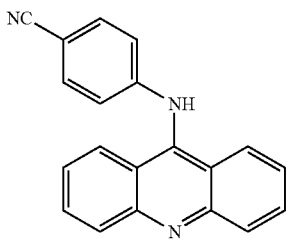

INVA3Z-30-1
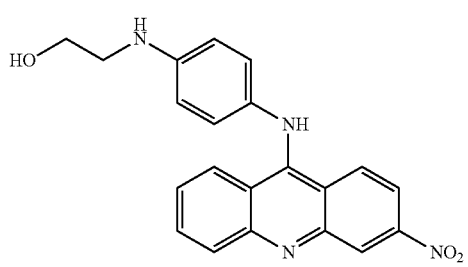
INVA3Z-30-3
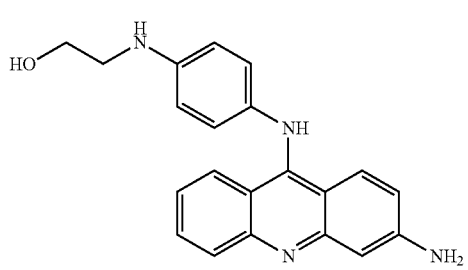
INVA3Z-31-1
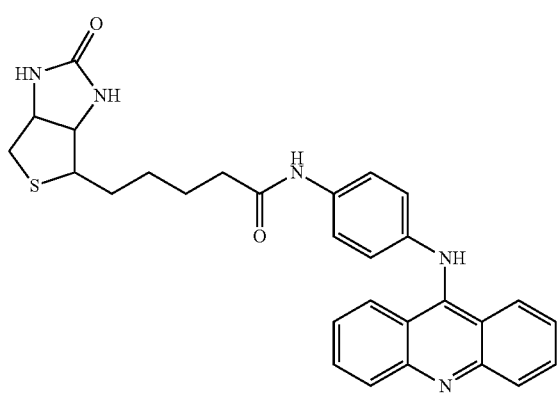
INVA3Z-32-1
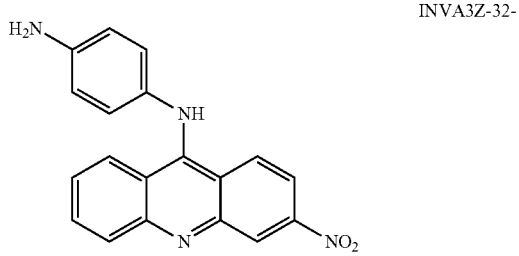
INVA3Z-32-2
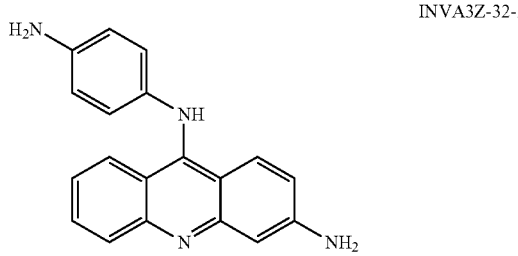
INVA3Z-36-1
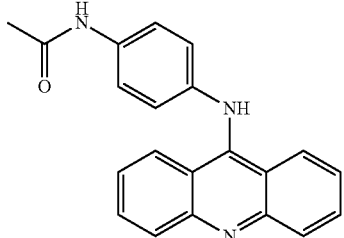
INVA3Z-37-1
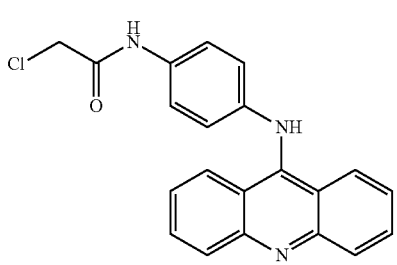
INVA3Z-38-1
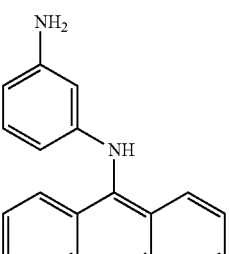
INVA3Z-39-1
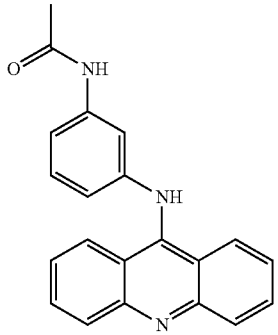
INVA3Z-40-1
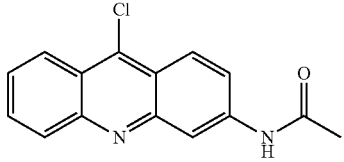
INVA3Z-40-2
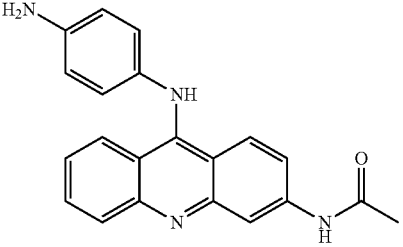

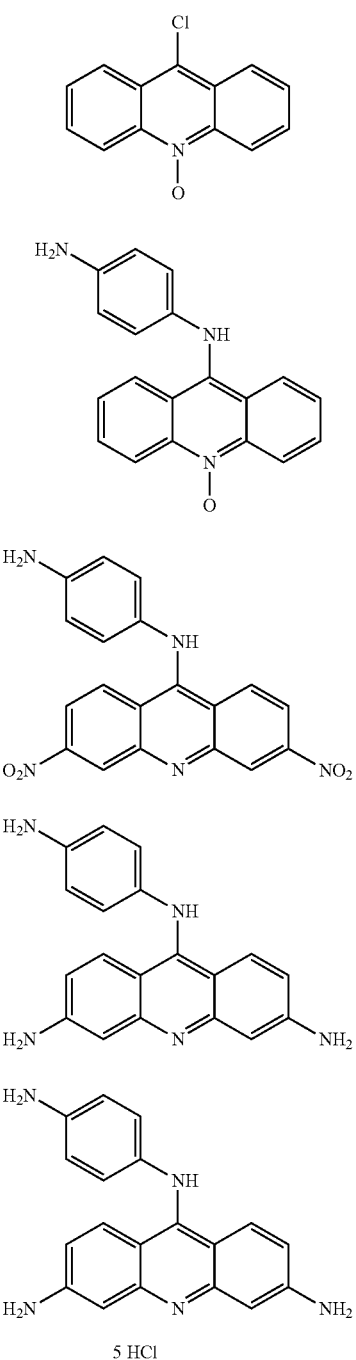

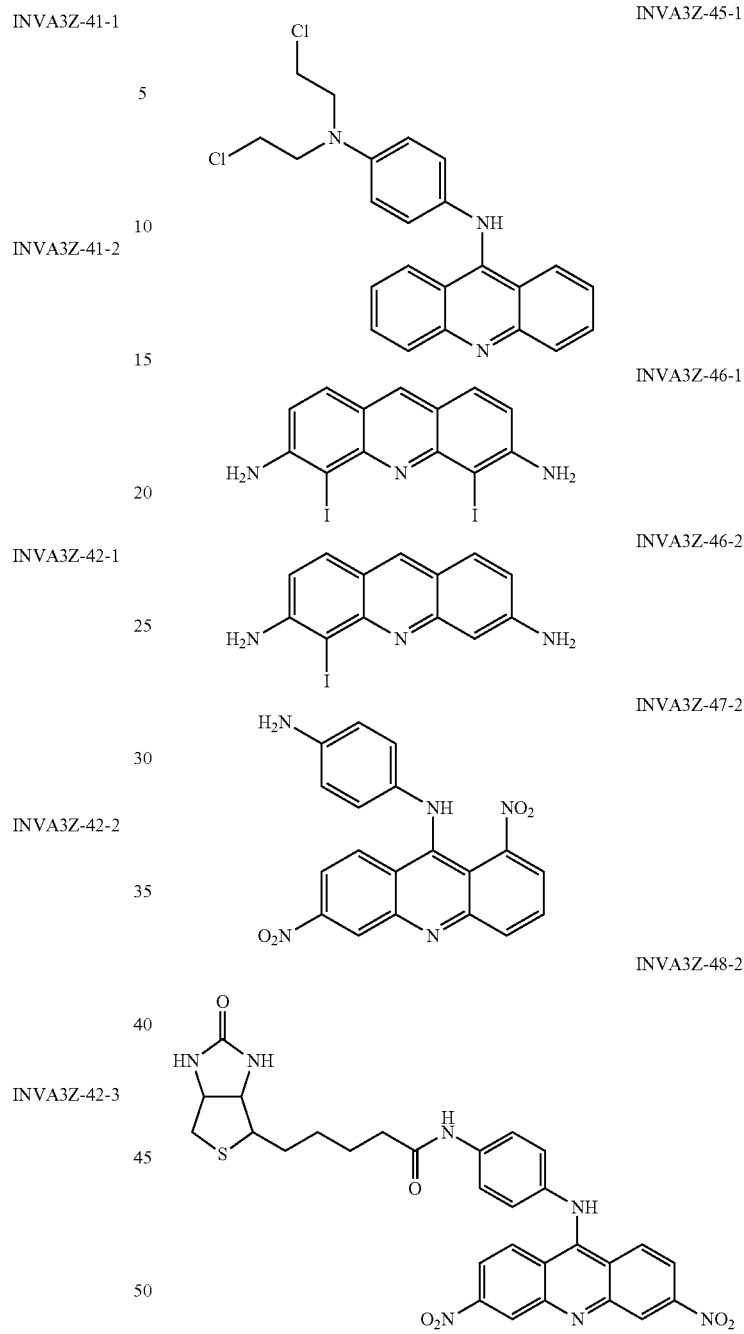

Activity of the Compounds

CTX1 and CTX50 Rapidly Induces p53 in a Non-DNA Damage Dependent Fashion:

CTX1 and CTX50 were selected as representative compounds for further analysis. These two selected compounds demonstrated several findings demonstrating strong molecules that can be develop towards anticancer drugs. For example CTX1 can induce p53 independently of DNA damage. CTX1, unlike doxorubicin (a well-known DNA damage agent) does not induce measurable DNA damage as measured by common markers of DNA damage (phosphorylation of α-H2AX or p53 (ser-15)) at doses necessary for p53 induction (FIG. 1A-B). Therefore, CTX1-mediated p53 induction was found to be independent of genotoxic stress.

CTX1 induces p53 rapidly supporting its direct role in stabilizing the p53 protein as opposed to induction by DNA damage or transcriptional mechanisms.

CTX1 and CTX50 Exhibits Specificity in Targeting HDMX:

Historically, targeting HDM2 was a focus to develop anti-cancer drug for several types of cancer having wild type P53 present. The basis behind targeting HDM2 is that the wild-type activities of p53 could be harnessed to induce apoptosis if HDM2 could be eliminated or dislodged from p53. Tumors that arise with properties permissive of p53 reactivation include those with inactivated upstream regulators, such as p14ARF, or overexpression of negative regulators, such as HDM2 or HDMX. Diverse approaches aimed at disrupting the interaction between HDM2 and p53 to facilitate wild-type p53 activities include the use of antibodies directed at HDM2, inhibitory peptides and anti-sense oligonucleotides or small-interfering RNAs to inhibit HDM2 expression (Patton. J T., et. al., Cancer research 66, 3169-3176 (2006), Hu. B., et. al., *The Journal of biological chemistry* 281, 33030-33035 (2006)). Perhaps the most promising approach is the potential to use low molecular weight compounds capable of disrupting the p53-HDM2 interaction such as nutlin-3 (Gurova. K V., et. al., *Proceedings of the National Academy of Sciences of the United States of America* 102, 17448-17453 (2005)). Nutlin compounds mimic the critical amino acids within the p53 alpha-helix that bind within the hydrophobic pocket of HDM2 where p53 normally resides, and show p53-specific antitumor properties in the low μM range (Ringshausen. I., et. al., *Cancer cell* 10, 501-514 (2006)). Studies surrounding Nutlin-3 have proven successful against B-cell chronic lymphocytic leukemia (B-CLL), multiple myeloma and AML, prompting discussion of a role for such antagonists in leukemia therapies (Graves. B., et. al. *Proceedings of the National Academy of Sciences of the United States of America* 109, 11788-11793 (2012), Bista. M., Et al., PloS one 7, e37518 (2012), Reed, D., Et. al., *The Journal of biological chemistry* 285, 10786-10796 (2010)). Currently there are several clinical trials in progress to evaluate an oral formulation of Nutlin-3 as an anticancer agent. As HDM2 inhibitors such as Nutlin-3 do not show efficacy on cancer cells that overexpress HDMX, the development of small molecules targeting HDMX is important. Towards this end our drug discovery effort identified HDMX inhibitor. To determine whether CTX1 is specific for overcoming p53 suppression due to HDMX, HDM2, or both, we utilized a fibroblast cell model system in which p53 was suppressed by HDMX or HDM2 overexpression. In addition as HDMX inhibition should partially lead to cell death through p53 induction, we also used cells in which p53 expression was knocked down. This same cell model system was previously shown to define the specificity of the HDM2 inhibitor, nutlin-3, for HDM2 (Chene. P., et. al. Nat Rev Cancer. 3 (2):102-9 (2003), Midgley. C A., et. al. Oncogene. 1997; 15 (10):1179-89 (1997)). CTX1 induced significant p53-dependent cell death in HDMX-expressing cells (Vector or HDMX), but not cells in which p53 is inactivated by HDM2 overexpression or when p53 is knocked down using p53 targeting shRNA (FIG. 2A). This study demonstrates CTX1 shows specificity in targeting HDMX over its homologue HDM2 also further supporting the ability of CTX1 to overcome HDMX-mediated p53 suppression. To further confirm the ability of CTX1 to overcome HDMX-mediated suppression of cell killing, we employed a leukemia cell model system. Consistent with the fibroblast cell model, OCI-AML3 (OCI) cells overexpressing HDMX were found to exhibit a similar sensitivity to CTX1 mediated cell killing as parental cells in contrast to the HDM2 inhibitor, nutlin-3, that demonstrates reduced activity in the presence of high HDMX levels (FIG. 2B-C).

CTX1 and CTX50 Can Directly Interact with HDMX and Modulates p53-HDMX Binding:

In order to explore how CTX1 leads to p53 induction, it was then assessed whether or not CTX1 can directly interact with HDMX and/or p53. In order to test for direct binding, a biotin-conjugated version of CTX1 was synthesized (FIG. 3A-B). The CTX1-biotin compound exhibits similar activity in cell killing to the parent compound. It was found that CTX1 can directly interact with GST-HDMX, but not unrelated proteins such as GST-FXR by immunoprecipitation (FIG. 3B). Biotin alone was confirmed not to bind with HDMX demonstrating the CTX1 component of the CTX1-biotin conjugate is responsible for this interaction.

In addition to testing the binding of CTX1 and HDMX through immunoprecipitations using biotin-tagged CTX1, the interaction of HDMX with non-tagged CTX1 was confirmed using two biophysical based approaches. The first utilized the fact that CTX1, but not HDMX exhibits a specific absorbance pattern that is detectable by a spectrophotometer. After co-incubation of CTX1 with HDMX (and removal of free CTX1 by size exclusion chromatography), not only does HDMX now exhibit an absorbance pattern, but there is also a clear spectral shift of the absorbance pattern as compared to free CTX1 (FIG. 3C and FIG. 4B). This spectral shift is highly suggestive of an HDMX/CTX1 interaction. In addition size exclusion chromatography performed on CTX1 alone as a control demonstrates the absorbance seen with the HDMX/CTX1 sample is not due to residual non-bound CTX1. Similar results observed when CTX1 was incubated with OCI cell and followed by either ELISA or immunoprecipitation experiments were performed (FIG. 3D and FIG. 4A)

Interestingly, CTX1 is an acridine containing molecule and other acridine containing compounds such as 9-aminoacridine (9-AA) have previously been shown to rapidly induce p53 in a non-DNA damage dependent fashion possibly related to its ability to intercalate in DNA (Graves. B., et. al. *Proceedings of the National Academy of Sciences of the United States of America* 109, 11788-11793 (2012)). Interestingly, binding of 9-AA to HDMX was not observed using the same spectral studies, suggesting a distinct mechanism of action (FIG. 3E).

Another biophysical approach confirmed HDMX and CTX1 binding. Using surface plasmon resonance (SPR), HDMX demonstrated strong binding to CTX1 (Kd 450 nM) but not nutlin-3 (Kd 5.1 μM) (FIG. 4C). Again 9-AA did not demonstrate any binding to HDMX using SPR at doses up to 12.5 μM.

In addition to observing interactions of CTX1 and HDMX, the ability of CTX1 to directly impair the interaction of p53 and HDMX, which could result in the observed stabilization of p53 protein, was assessed. Utilizing an ELISA assay, it was found that CTX1 disrupted HDMX/p53, but not HDM2/p53 interactions (FIG. 4A). In contrast the HDM2 inhibitor, nutlin-3, disrupts the interaction between p53 and HDM2, but not p53 and HDMX. This result suggests that CTX1's ability to impair HDMX/p53 binding is specific and is not simply due to its acridine moiety. Identical results were obtained when CTX50 was used in several similar experiments were performed; few results are shown in FIG. 4D.

CTX1 and its Analogue Impairs Cancer Cell Growth:

In order to explore the effects of CTX1 on cancer cell growth and survival, the ability of CTX1 to inhibit the growth and/or kill a panel of wild-type p53 cancer cell lines (including HCT116, A549, MCF7, LNCaP, OCI-AML3 (OCI), and MOLM-3 (FIG. 5)) was tested. Various analogues were found to exhibit growth inhibition and killing preferentially on wild type p53 expressing cells as well as synergistic or additive killing when combined with nutlin-3, in the following table we provided cell killing activity towards a particular cell lines OCI (Table 1)

TABLE 1

$IC_{50}$ values of representative analogues, values are determined based on OCI cell line.

| ID | IC 50 μM |
| --- | --- |
| INVA3Z-1-1 | 13.5 |
| INVA3Z-6-1 | 14.1 |
| INVA3Z-6-3 | 13.4 |
| INVA3Z-10-1 | 9.8 |
| INVA3Z-13-1 | 9.9 |
| INVA3Z-14-1 | 4.2 |
| INVA3Z-17-2 | 13.6 |
| INVA3Z-5-2 | 4.7 |
| INVA3Z-19-1 | 5.8 |
| INVA3Z-21-2 | 6.3 |
| INVA3Z-23-2 | 14.2 |
| INVA3Z-24-2 | >8.0 |
| INVA3Z-26-3 | >8.0 |
| INVA3Z-28-1 | 7.8 |
| INVA3Z-29-1 | >8 |
| INVA3Z-29-2 | >8 |
| INVA3Z-30-1 | >8 |
| INVA3Z-30-3 | 4.8 |
| INVA3Z-31-1 | 11.9 |
| INVA3Z-32-1 | 4.8 |
| INVA3Z-32-2 | 4.7 |
| INVA3Z-36-1 | 4.9 |
| INVA3Z-37-1 | 4.6 |
| INVA3Z-38-1 | 11.8 |
| INVA3Z-39-1 | 12.1 |
| INVA3Z-40-1 | 13.2 |
| INVA3Z-40-2 | 13.9 |
| INVA3Z-41-1 | >15 |
| INVA3Z-41-2 | 14.3 |
| INVA3Z-42-1 | 0.13 |
| INVA3Z-42-2 | 14.4 |
| INVA3Z-43-1 | 11.9 |
| INVA3Z-44-1 | >15 |
| INVA3Z-45-1 | 13.7 |
| INVA3Z-46-1 | 8.3 |
| INVA3Z-46-2 | 7.9 |
| INVA3Z-47-2 | 9.5 |
| INVA3Z-48-2 | 8.2 |
| INVA3Z-49-2 | 8.4 |
| INVA3Z-50-1 | 6.3 |
| INVA3Z-50-2 | 1.4 |
| INVA3Z-51-1 | 11.8 |
| INVA3Z-51-2 | >15 |
| INVA3Z-52-3 | 7.8 |
| INVA3Z-52-2 | 3.4 |
| INVA3Z-53-2 | 3.2 |
| INVA3Z-54-1 | 10.2 |
| INVA3Z-54-2 | 8.1 |
| INVA3-55-2 | 4.3 |
| INVA3Z-55-1 | 3.2 |
| INVA3-MG-1C | 5.4 |
| INVA3-MG-2B | 4.8 |
| INVA3-MG-3B | 7.5 |
| INVA3-MG-4D | 15 |
| INVA3Z-56-1 | 1.8 |
| INVA3Z-58-1 | >15 |
| INVA3Z-58-2 | >15 |
| INVA3Z-59-2 | 12.8 |
| INVA3Z-60-2 | >15 |
| INVA3Z-60-3 | 10.2 |
| INVA3Z-61-1 | 1.4 |
| INVA3Z-61-2 | 4.3 |
| INVA3-62-1 | — |
| INVA3Z-62-2 | 9.5 |

TABLE 1-continued $IC_{50}$ values of representative analogues, values are determined based on OCI cell line.

| ID | IC 50 μM |
| --- | --- |
| INVA3Z-63-1 | >15 |
| INVA3Z-63-2 | >15 |
| INVA3Z-64-1 | >15 |
| INVA3Z-64-3 | >15 |
| INVA3Z-65-1 | 12.9 |
| INVA3Z-65-2 | 11.5 |
| INVA3Z-66-1 | >15 |
| INVA3Z-66-2 | 8.4 |
| INVA3Z-67-1 | 7.3 |

CTX1 and CTX50 Specifically p53 Positive Cancer Cells

Cell cycle analysis of paired p53-expressing and p53-deficient cancer cell lines (HCT116 and A549) also demonstrates that CTX1 mediates growth inhibition partially through a p53-dependent pathway. For example, after 24 hr of treatment with CTX1 in HCT116 p53-wild-type cells there is a decrease in S phase from 20% to 4% while HCT116 p53-null cells exhibit a reduction in S phase from 25% to 15% (FIG. 6A-B). To further characterize the mechanism of cell killing Annexin-V staining was done to assess for apoptosis in HCT116 p53-wild type and p53-null cells. Again the combination of CTX1 and nutlin-3 led to a synergistic induction of apoptosis in p53-wild type, but not p53-null cells (FIG. 7A-B).

CTX1 Exhibits High in Vivo Anti-tumor Activity:

As CTX1 represents one of the few examples of a compound that can induce p53 and kill cancer cells in a genotoxic-independent fashion, mouse efficacy studies were performed in order to begin to explore its clinical potential. A highly aggressive AML model system was used for this study as this is a disease unlike most malignancies in which wild-type p53 status is extremely common and new therapeutics are urgently needed. The ability of CTX1 (30 mg/kg i.p.), nutlin-3 (200 mg/kg p.o.) or the combination to impact the growth of primary human AML cells in immunodeficient mice was assessed. This model system closely mimics the human disease as primary patient samples can be utilized and the leukemic cells circulate in the mouse and proliferate in the bone marrow. Utilizing a primary human AML sample (derived from a patient with refractory and relapsed AML), we found that CTX1 even as a single agent significantly enhanced the survival of mice in this model system (FIG. 8). Of note this model system is clinically important as there is no existing therapeutics that is efficacious in this patient population. While all of the vehicle mice succumbed to disease by 60 days after cell injection, mice treated with CTX1 alone or in combination with nutlin-3 had a significantly increased survival time. Also of note, the standard AML therapeutic cytarabine does not demonstrate efficacy in this model system.

The foregoing descriptions of various embodiments provide illustration of the inventive concepts. The descriptions are not intended to be exhaustive or to limit the disclosed invention to the precise form disclosed. Modifications or variations are also possible in light of the above teachings. The embodiments described above were chosen to provide the best application to thereby enable one of ordinary skill in the art to utilize the inventions in various embodiments and with various modifications as are suited to the particular use contemplated. All such modifications and variations are within the scope of the invention. All publications, patents and patent applications referenced herein are to be each individually considered to be incorporated by reference in their entirety.

We claim:
1. A compound comprising the structure of:

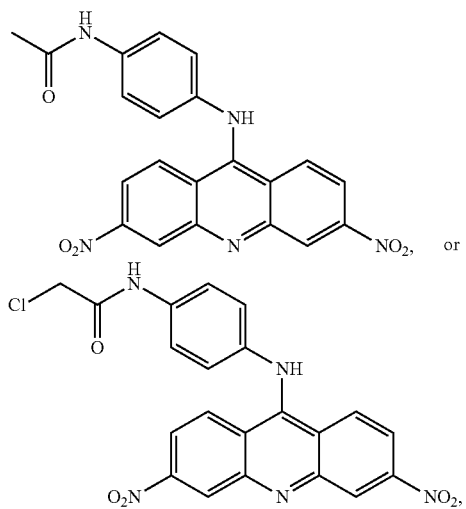

or a salt thereof.

2. A pharmaceutical compound comprising the compound of claim 1 and a pharmaceutically acceptable carrier.

3. A method of inducing apoptosis in a cell, comprising administering the compound of claim 1 to a cell, wherein the compound antagonizes HDMX activity toward p53.

4. The method of claim 3, wherein the cell is within a subject.

5. The method of claim 3, further comprising selecting for increased HDMX activity within the cell.

6. The method of claim 3, further comprising selecting the cell for reduced p53 activity.

7. The method of claim 5, further comprising selecting for increased HDM2 activity.

8. The method of claim 7, further comprising administering nutilin-3 to the cell.

9. The method of claim 3, further comprising selecting the cell for increased HDMX activity and HDM2 activity and administering nutilin-3 in combination with the compound.

10. A method of treating a cancerous cell comprising administering the compound of claim 1 to a cancerous cell.

11. The method of claim 10, wherein the cancerous cell is within a subject.

12. The method of claim 11, wherein the subject is a human.

13. The method of claim 12, wherein the compound is administered by inhalation, injection or oral administration.

14. The method of claim 10, wherein the cancerous cell is selected for reduced p53 activity.

* * * * *